(12) United States Patent
Kovacs et al.

(10) Patent No.: US 8,273,029 B2
(45) Date of Patent: Sep. 25, 2012

(54) PRESSURE RECOVERY INDEX TO ASSESS CARDIAC FUNCTION

(75) Inventors: Sandor J. Kovacs, St. Louis, MO (US); Leonid Shmuylovich, St. Louis, MO (US); Wei Zhang, St. Louis, MO (US); Charles Chung, Tucson, AZ (US)

(73) Assignee: Washington University, St. Louis, MO (US)

( * ) Notice: Subject to any disclaimer, the term of this patent is extended or adjusted under 35 U.S.C. 154(b) by 713 days.

(21) Appl. No.: 12/372,512

(22) Filed: Feb. 17, 2009

(65) Prior Publication Data

US 2009/0209869 A1    Aug. 20, 2009

Related U.S. Application Data

(60) Provisional application No. 61/029,505, filed on Feb. 18, 2008.

(51) Int. Cl.
*A61B 6/00* (2006.01)
*A61B 5/02* (2006.01)

(52) U.S. Cl. ........ 600/481; 600/479; 600/480; 600/485; 600/486; 600/508; 600/516; 600/517; 600/526

(58) Field of Classification Search .......... 600/479, 600/480, 481, 485, 486, 508, 516, 517, 526
See application file for complete search history.

(56) References Cited

U.S. PATENT DOCUMENTS

| | | | |
|---|---|---|---|
| 5,743,267 A | 4/1998 | Nikolic et al. | |
| 5,743,268 A | 4/1998 | Kabal | |
| 6,544,181 B1 | 4/2003 | Buck et al. | |
| 6,610,018 B1 | 8/2003 | McIntyre | |
| 6,795,732 B2 | 9/2004 | Stadler | |
| 7,022,077 B2 | 4/2006 | Mourad et al. | |
| 7,054,679 B2 | 5/2006 | Hirsh | |
| 7,233,821 B2 | 6/2007 | Hettrick et al. | |
| 2005/0203429 A1 | 9/2005 | Judy | |
| 2006/0287604 A1 | 12/2006 | Hickey | |
| 2007/0049824 A1 | 3/2007 | Konofagou et al. | |

OTHER PUBLICATIONS

Lisauskas et al. Chamber properties from transmitral flow: prediction of average and passive left ventricular diastolic fluctuations. J. Appl. Physiol. 91: 154-162 (2001).*

Rankin J.S., et al., Viscoelastic Properties of the Diastolic Left Ventricle in the Conscious Dog, Journal of the American Heart Association, Circulation Research, 1977, pp. 37-45, vol. 41, American Heart Association, USA.

Nikolic, S.D., et al., Diastolic Viscous Properties of the Intact Canine Left Ventricle, Journal of the American Heart Association, Circulation Research, 1990, pp. 352-359, vol. 67, American Heart Association, USA.

(Continued)

*Primary Examiner* — Gail R Gabel
(74) *Attorney, Agent, or Firm* — Armstrong Teasdale LLP

(57) ABSTRACT

Determining an index for assessing cardiac function. In an embodiment, a method includes receiving ventricular pressure data during an invasive cardiac procedure, wherein the received pressure data includes a diastatic ventricular pressure value, a minimum ventricular pressure value, and a predefined fiducial marker pressure value. An index value is calculated by comparing a first pressure difference to a second pressure difference. The first pressure difference represents the difference between the received diastatic ventricular pressure value and the received minimum ventricular pressure value. The second pressure difference represents the difference between the received fiducial marker pressure value and the received minimum ventricular pressure value. The index value is provided to a health care provider to assess early diastolic cardiac function.

6 Claims, 20 Drawing Sheets

OTHER PUBLICATIONS

Murakami, T., et al., Diastolic Filling Dynamics in Patients with Aortic Stenosis, Journal of the American Heart Association, Circulation, 1986, pp. 1162-1174, vol. 73, American Heart Association, USA.

Matsubara, et al., Logistic Time Constant of Isovolumic Relaxation Pressure—Time Curve in the Canine Left Ventricle, Circulation, 1995, pp. 2318 2326, vol. 92, American Heart Association, USA.

Chung, Charles S., et al., Isovolumic Pressure-to-Early Rapid Filling Decay Rate Relation: Model-Based Derivation and Validation via Simultaneous Catheterization Echocardiography, J Appl Physiol, Oct. 13, 2005, pp. 528-534, vol. 100, The American Physiological Society, USA.

Chung, Charles S., et al., Duration of Diastole and its Phases as a Function of Heart Rate During Supine Bicycle Exercise, Am J Physiol Heart Circ, 2004, pp. 2003-2008, vol. 287, The American Physiological Society, USA.

Cheng, C. P., et al., Mechanism of Augmented Rate of Left Ventricular Filling During Exercise, Journal of the American Heart Association, 1992, pp. 9-19, vol. 70, American Heart Association, USA.

Bauman, Lisa, et al., The Peak Atrioventricular Pressure Gradient to Transmitral Flow Relation: Kinematic Model Prediction with In Vivo Validation, The Cardiovascular Biophysics Laboratory, Cardiovascular Division, Washington University School of Medicine, 2004, pp. 839-844, The American Society of Echocardiography, USA.

Appleton, Christopher P., The Echo-Doppler Evaluation of Left Ventricular Diastolic Function a Current Perspective, 2000, 34 Pages, vol. 18, Issue 3, W.B. Saunders Company, USA.

Little, William C., et al., Determination of Left Ventricular Chamber Stiffness From the Time for Deceleration of Early Left Ventricular Filing, Circulation, 1995, pp. 1933-1939, vol. 92, American Heart Association, Inc., USA.

Lisauskas, Jennifer B., et al., Chamber Properties from Transmitral Flow: Prediction of Average and Passive Left Ventricular Diastolic Stiffness, 2001, pp. 154-162, vol. 91, The American Physiological Society, USA.

Kulke, M., et al., Interaction Between PEVK-Titin and Actin Filaments. Origin of a Viscous Force Component in Cardiac Myofibrils, 2001, pp. 1-16, American Heart Association, USA.

Kovacs, Sandor J., et al., Evaluation of Diastolic Function with Doppler Echocardiography: the PDF Formalism, 1987, pp. 178-187, The American Physiological Society, USA.

Kheradvar, Arash, et al., Assessment of Left Ventricular Viscoelastic Components Based on Ventricular Harmonic Behavior, Cardiovascular Engineering: An International Journal, 2006, pp. 31-40, vol. 6, No. 1, Springer Science and Business Media, Inc., USA.

Zhang, Wei, et al., the Kinematic Filling Efficiency Index of the Left Ventricle: Contrasting Normal vs. Diabetic Physiology, National Institute of Health, Author Manuscript, 2007, pp. 842-850, vol. 33, Issue 6, Ultrasound Med. Biol., USA.

Yellin, E.L., et al., The Influence of Left Ventricular Filling on Postextrasystolic Potentiation in the Dog, Journal of the American Heart Association, Circulation Research, 1979, pp. 712-722, vol. 44, American Heart Association, USA.

Weiss, James L., et al., Hemodynamic Determinants of the Time-Course of Fall in Canine Left Ventricular Pressure, 1976, pp. 751-760, vol. 58, The Journal of Clinical Investigation, USA.

Templeton, Gordon H., et al., Elastic and Viscous Stiffness of the Canine Left Ventricle, 1974, pp. 123-127, vol. 36, No. 1, Journal of Applied Physiology, USA.

Starc, Vito, et al., Viscoelastic Behavior of the Isolated Guinea Pig Left Ventricle in Diastole, 1996, pp. 1314-1324, The American Physiological Society, USA.

Shmuylovich, Leonid, et al., E-Wave Decleration Time May Not Provide an Accurate Determination of LV Chamber Stiffness if LV Relaxation/Viscoelasticity is Unknown, Am. J. Physiol. Heart Circ. Physiol., 2007, pp. 2712-2720, vol. 292, The American Physiological Society, USA.

Riordan, Matt M., et al., Diabetes and Diastolic Function: Stiffness and Relaxation From Transmitral Flow, World Federation for Ultrasound in Medincine and Biology, 2005, pp. 1589-1596, vol. 31, No. 12, Elsevier, USA.

Kass, David A., Assessment of Diastolic Dysfunction Invasive Modalities, Cardiology Clinics Medical Journal, 2000, pp. 1-16, vol. 18, Issue 3, W.B. Saunders Company, USA.

Hess, O. M., et al., Diastolic Simple Elastic and Viscoelastic Properties of the Left Ventricle in Man, Journal of the American Heart Association, Circulation, 1979, pp. 1178-1187, vol. 59, American Heart Association, USA.

Ewert, Dan, et al., The Effect of Heart Rate, Preload, and Afterload on the Viscoelastic Properties of the Swine Myocardium, Annals of Biomedical Engineering, 2004, pp. 1211-1222, vol. 32, No. 9, biomedical Engineering Society, USA.

Courtois, M., et al., Transmitral Pressure-Flow Velocity Relation, Importance of Regional Pressure Gradients in the Left Ventricle During Diastole, Journal of the American Heart Association, Circulation, 1988, pp. 661-671, vol. 78, American Heart Association, USA.

Yang, S.S., et al., From Cardiac Catheterization Data to Hemodyamic Parameters, Philadelphia, F.A. Davis 1988, pp. 122-151.

Miki, S., et al., Doppler Echocardiographic Transmitral Peak Early Velocity Does Not Directly Reflect Hemodynamic Changes in Humans of Normalization to Mitral Stroke Volume, Journal of American College of Cardiology, 1991, pp. 1507-1516, vol. 17, American College of Cardiology, USA.

Wang, J., et al., Current Perspectives on Cardiac Function in Patients with Diastolic Heart Failure, Journal of the American Heart Association, Circulation, 2009, pp. 1146-1157, vol. 119, American Heart Association, USA.

Thomas, J.D., et al., Isovolumic Relaxation Time Varies Predictably with its Time Constant and Aortic and Left Atrial Pressures: Implications for the Noninvasive Evaluation of Ventricular Relaxation, American Heart Journal, 1992, pp. 1305-1313, vol. 124, Issue 5, American Heart Association, USA.

Stoddard, M.F, et al., The Effect of Premature Ventricular Contraction on Left Ventricular Relaxation, Chamber Stiffness, and Filling in Humans, American Heart Journal, 1989, pp. 725-733, vol. 118, Issue 4, American Heart Association, USA.

\* cited by examiner

PRESSURE RECOVERY INDEX TO ASSESS CARDIAC FUNCTION

CROSS REFERENCE TO RELATED APPLICATIONS

This application claims the benefit of U.S. Provisional Application No. 61/029,505 filed Feb. 18, 2008, which is hereby incorporated by reference in its entirety.

BACKGROUND

The time constant of isovolumic relaxation ($\tau$), and the transmitral Doppler E-wave deceleration time (DT) are typically used to characterize relaxation-related, diastolic left ventricular (LV) properties. DT may be assessed during routine studies or after a Valsalva maneuver for "pseudonormalized" E-wave patterns. When DT is prolonged and a Doppler E-wave peak velocity is lower than a Doppler A-wave peak velocity, the transmitral flow contour is said to possess a delayed relaxation pattern (DR). A DR pattern is an established hallmark of LV diastolic dysfunction. However, two LV chambers having indistinguishable $\tau$ and indistinguishable stiffness ($\Delta P/\Delta V$) can have significantly different DT. Furthermore, subjects with and without the DR pattern on echocardiography may have indistinguishable $\tau$ values. Thus, $\tau$ provides an incomplete characterization of relaxation during early-rapid filling. A mechanism for determining an invasive early-rapid filling index of LV relaxation/viscoelasticity that effectively correlates to the DR pattern is lacking in the art.

SUMMARY

Embodiments of the invention receive ventricular pressure data during an invasive cardiac procedure, wherein the received pressure data includes a diastatic ventricular pressure value, a minimum ventricular pressure value, and a predefined fiducial marker ventricular pressure value. A first pressure difference between the received diastatic ventricular pressure value and the received minimum ventricular pressure value is determined. A second pressure difference between the received fiducial marker ventricular pressure value and the received minimum ventricular pressure value is determined. The first and second pressure differences are compared to generate an index value indicative of early diastolic cardiac function. The generated index value is provided to a health care provider to assess cardiac function.

BRIEF DESCRIPTION OF THE DRAWINGS

Aspects of the invention may be better understood by referring to the following descriptions in conjunction with the accompanying drawings.

Corresponding reference characters indicate corresponding parts throughout the drawings.

DETAILED DESCRIPTION

Embodiments of the invention provide an assessment of cardiac function during early filling using invasively-acquired data. In an embodiment, the assessment is based on a ratio of pressure differences calculated from pressure data obtained during catheterization.

Figure 1:
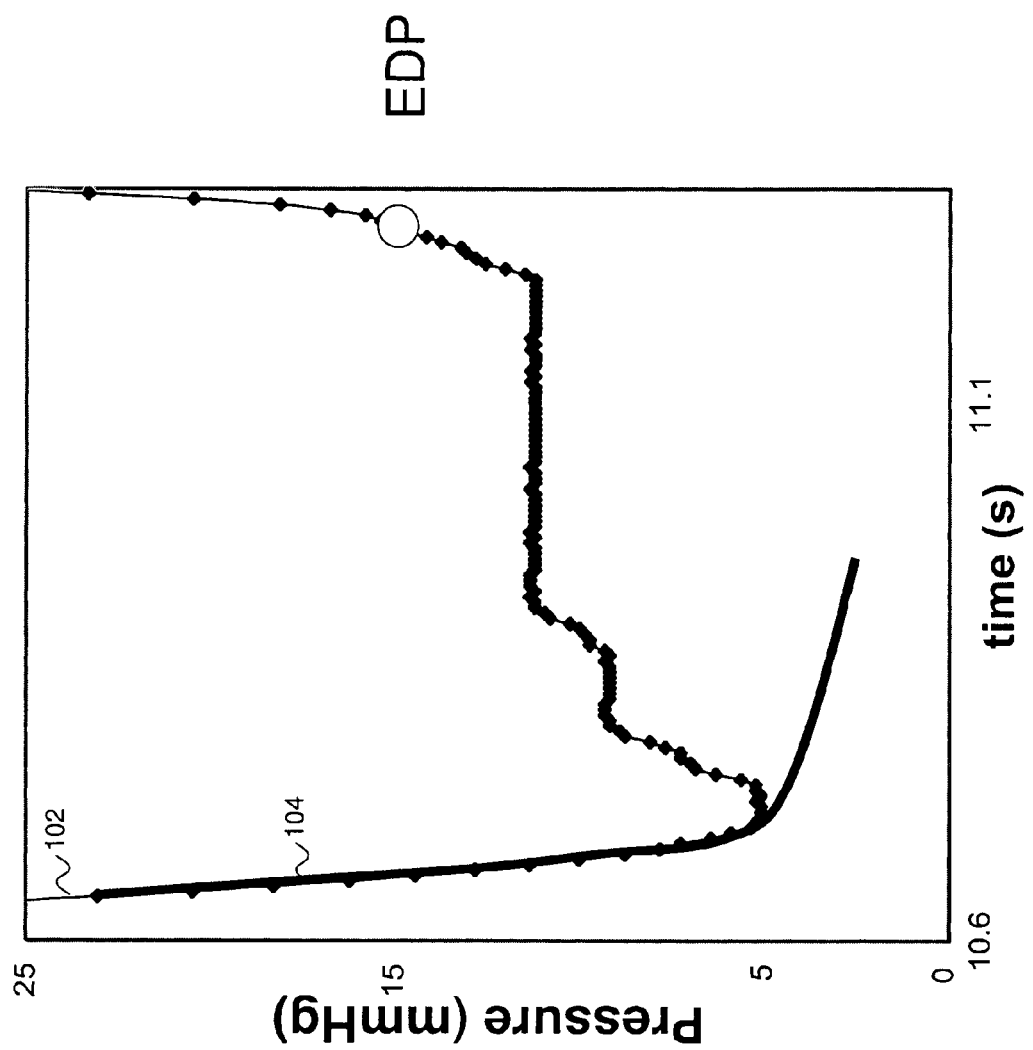
FIG. 1 is a graph showing an exemplary left ventricular pressure decline empirically fit by an assumed exponential decay with a relaxation time-constant, $\tau$.
Figure 2:
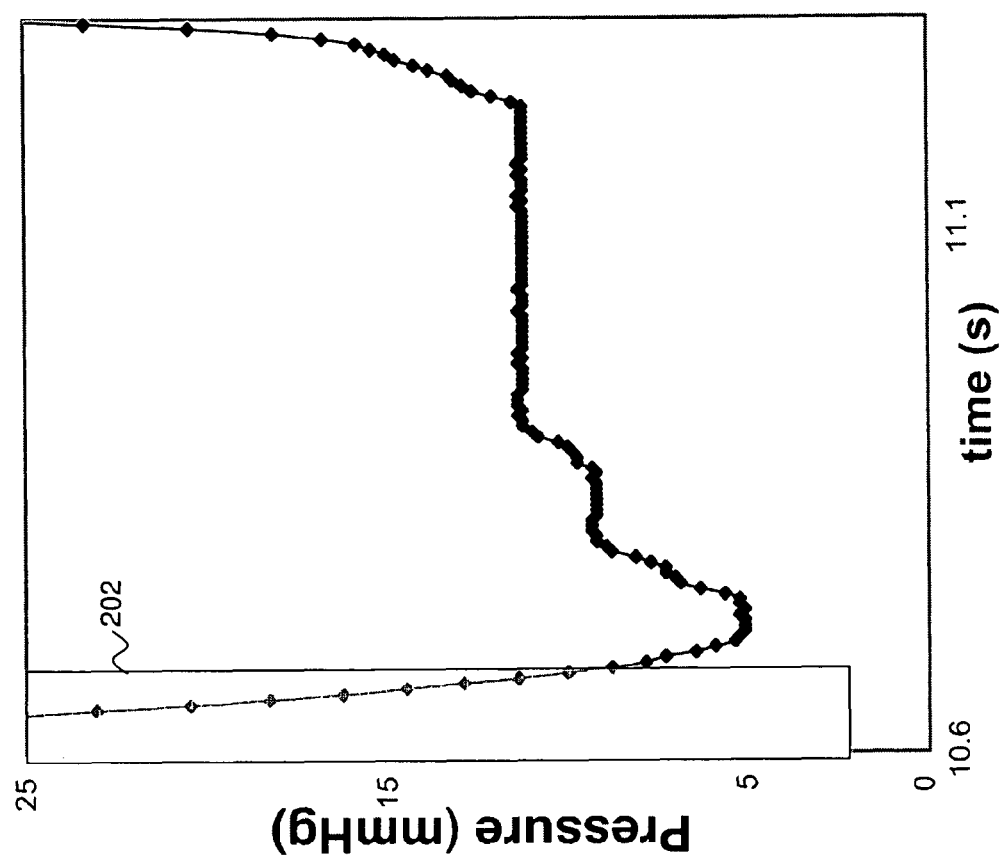
FIG. 2 is a graph showing an exemplary left ventricular pressure decline and a measurement interval for an index of relaxation, $\tau$.
Figure 3:
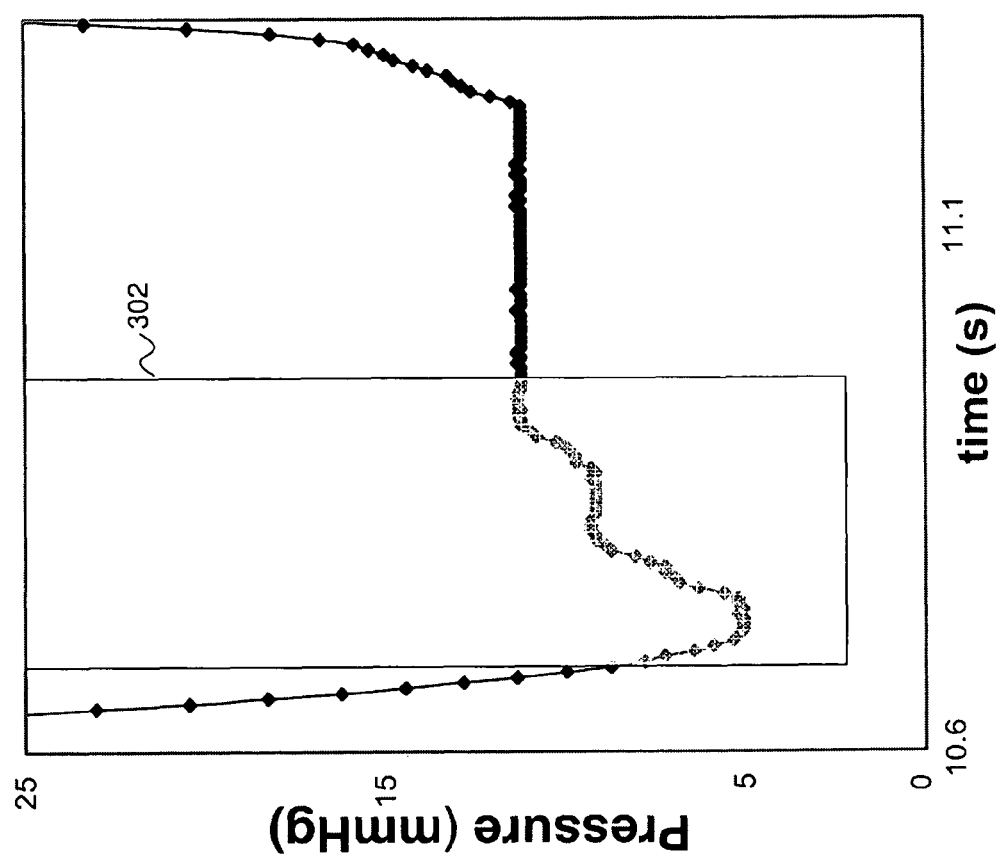
FIG. 3 is a graph showing an exemplary left ventricular pressure decline and an index measurement interval during a Doppler E-wave.

Each year cardiologists perform hundreds of thousands of diagnostic cardiac catheterizations in which pressure in the left ventricle is recorded. Each heart chamber, such as the left ventricle, is understood to have relaxation and stiffness properties that are used to differentiate one patient from another or to make diagnoses and treatment decisions based on the diagnoses. Current methods of measuring relaxation and stiffness include measuring left ventricular end-diastolic pressure (LVEDP) and determine an isovolumic relaxation constant ($\tau$). The computation of $\tau$ requires a mathematical fit to the pressure contour so it is rarely mentioned in the routine clinical catheterization report. Using Doppler-echocardiography to measure transmitral flow velocities (e.g., E-waves and A-waves), non-invasive information concerning the stiffness of the left ventricle and filling-related relaxation properties of the left ventricle may be used to further assess left ventricular function. Patients exhibiting a delayed relaxation pattern, for example, wherein the E-wave duration is prolonged and lower in peak value than the A-wave peak, often have underlying diastolic dysfunction. Furthermore, when the relaxation/viscoelasticity index, c, of the left ventricle is abnormal it may be a sign of impaired left ventricle functionality as is seen in disease states such as ischemia, hypertension, or diabetes. As shown in FIG. 1, left ventricular pressure decline 102 is empirically fit by an assumed exponential decay 104, with a time constant of $\tau$. In addition, as shown in FIG. 2, the current invasive index of relaxation, $\tau$, is determined by isovolumic relaxation of LVP, the shaded interval 202, which ends before the filling begins. The embodiments described herein describe an index determined by LVP that applies during early rapid filling of the left ventricle, i.e., during a Doppler E-wave, which corresponds to the shaded area 302 shown in FIG. 3.

Given the acknowledged epidemic of heart failure with normal ejection fraction, the medical community has become increasingly aware of the importance of quantitative characterization of diastolic function (DF). Both invasive modalities, such as catheterization, and non-invasive modalities, such as magnetic resonance imaging, nuclear cardiology, echocardiography, CT scanning etc., may be used to quantitatively and qualitatively characterize DF and diastolic dysfunction (DD). Two distinct chamber properties, stiffness and relaxation, are often used to characterize how the heart works when it fills and thereby determine DF. In dimensional terms, stiffness ($\Delta P/\Delta V$) is the change in pressure per unit of change in volume. It is defined in an embodiment as the slope between points on the diastolic portion of the pressure-volume (PV) loop, or by the slope of the end-diastolic pressure volume relationship (EDPVR) or by the slope of the diastatic pressure-volume relation (D-PVR). Either of the measured slope values is typically measured as an average over many beats. Relaxation is quantified during catheterization via $\tau$ or $\tau_L$, the time-constant or logistic time-constant of isovolumic relaxation (IVR), and echocardiographically by either the isovolumic relaxation time (IVRT) or the deceleration time (DT) of the transmitral Doppler E-wave.

Figure 4:
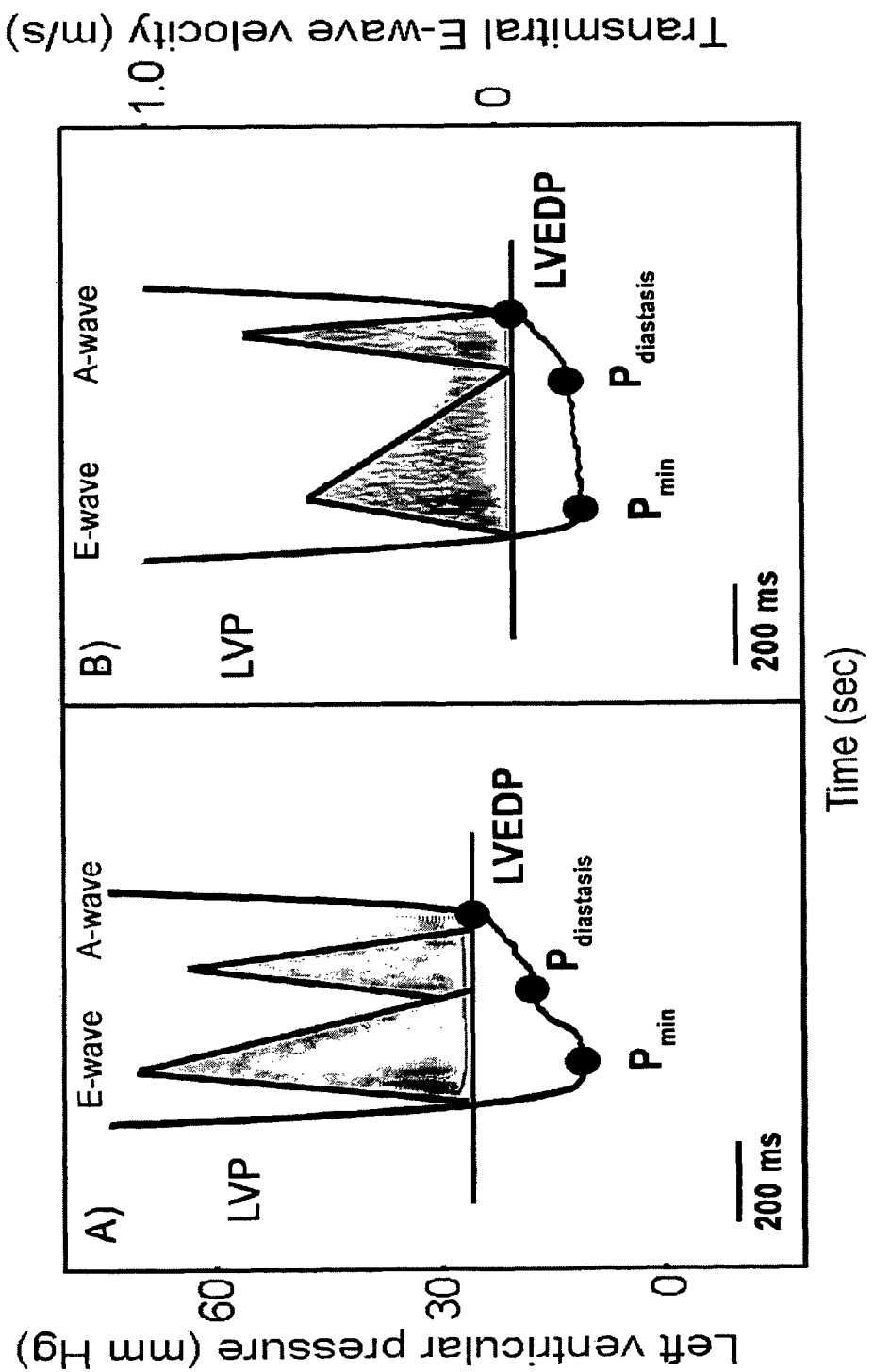
FIG. 4 is a graph showing exemplary simultaneous transmitral flow (e.g., Doppler echo) and micromanometric left ventricular pressure (LVP) from two subjects with statistically indistinguishable isovolumic relaxation (IVR) time constant ($\tau$), ($\Delta P/\Delta V$)$_{AVG}$, and similar ejection fraction (EF), but significantly different deceleration time (DT) and filling pattern.

In current clinical practice, the ability of the ventricle to relax is measured before the mitral valve opens and filling begins. However, relaxation properties of the ventricle also manifest declare themselves during filling, and in current clinical practice there is no method by which invasively acquired left ventricular pressure data can be used to derive relaxation and/or viscoelastic chamber properties during early, rapid filling. Moreover, in current clinical practice, assessment of diastolic function involves the determination of ventricular relaxation and stiffness parameters. Using invasive modalities, clinicians can measure $\tau$, the time-constant of isovolumic relaxation. Concomitantly clinicians may determine noninvasively whether transmitral flow E-waves exhibit a delayed relaxation pattern or not, or determine whether the DTI determined E'-wave is oscillatory or not. Absence of oscillation of E' is a correlate of abnormal relaxation. Many patients with prolonged $\tau$ have delayed relaxation E-wave patterns. However, these two measures are not always concordant and their causal relationship is complex. FIG. 4 shows an example of two subjects having indistinguishable $\tau$ and LVEF, but distinguishable DT. More specifically, FIG. 4 shows a simultaneous transmitral flow (Doppler echo) and micromanometric LVP from two subjects with statistically indistinguishable isovolumic relaxation time constant ($\tau$), $\Delta P/\Delta V_{AVG}$, and similar ejection fraction (EF), but significantly different deceleration time (DT). Furthermore, despite indistinguishable $\tau$ values between subjects, subject 2 possesses a delayed relaxation pattern, while subject 1 possesses normal E-wave and A-wave patterns. One representative heart beat from each subject is shown. The first patient's data, shown in graph A of FIG. 4, includes a cardiac cycle with $\tau$=52 ms, DT=204 ms, EF=80%. The second patient's data, shown as graph B of FIG. 4 includes a cardiac cycle with the similar $\tau$=49 ms, DT=304 ms, EF=73%.

An alternative explanation that may be offered for the data in FIG. 4 is that because DT is often used as a noninvasive measure of stiffness, the findings of FIG. 4 are best explained by different ventricular stiffness between subjects. However, for the subjects selected for FIG. 4 the values for invasively measured chamber stiffness are also indistinguishable. Furthermore, DT is generally a function of both stiffness and viscoelasticity/relaxation. It is therefore reasonable to conclude that $\tau$ does not fully capture the relaxation/viscoelastic properties which declare themselves beyond isovolumic relaxation and are lumped into DT. Therefore, the search for an invasive parameter that more accurately reflects ventricular relaxation/viscoelasticity beyond the isovolumic relaxation is justified, particularly when prolonged DT and the delayed relaxation pattern is encountered.

Numerous studies have established that during filling the ventricle behaves as a viscoelastic material. In accordance with current clinical definitions of stiffness, elastic chamber properties have been determined via the slopes of PV-relationships under selected pathologic and experimental conditions. However, the current clinically used measures of relaxation do not neatly map onto classic physiological studies of viscous ventricular properties. Indeed, current invasively defined clinical measures of relaxation are derived by fitting an assumed exponential decay or logistic equation exclusively to the isovolumic portion of the left ventricular pressure (LVP) signal. Thus, while important contributions have been made towards characterizing chamber relaxation/viscoelasticity in diastole, the in-vivo determination of relaxation/viscoelastic attributes has not been extended beyond isovolumic relaxation.

Others have previously proposed invasive indexes of viscoelasticity beyond the interval where $\tau$ is determined. For example, a sinusoidal volume variation may be applied to an isolated ventricular chamber and a viscoelastic property may be measured by the phase delay of the resulting pressure response. Furthermore, it has been shown that ventricular stiffness has two components, an elastic component measured by $\Delta P/\Delta V$, and a viscous component measured by the phase difference between the hemodynamic pressure and the volume signal. Additionally, it is known that in order to fit the stress strain relation of the ventricle obtained in open chest dog hearts, a viscoelastic, rather than elastic only, model is needed. Similar results have been reported in humans. Other investigators have observed viscoelastic chamber properties in various experimental settings. However, few of these studies are carried out in closed-chest, in-vivo ventricular chambers under normal physiologic conditions using routine clinical methods.

Several noninvasive indexes related to relaxation/viscoelasticity have been studied. The Doppler derived isovolumic relaxation time (IVRT) provides a robust estimate of the time required for isovolumic relaxation defined by the interval between aortic valve closure and mitral valve opening. IVRT, in addition to E-wave DT, when measured in subjects without constrictive-restrictive E-wave patterns, reflects relaxation properties of the ventricle.

A heart chamber's relaxation/viscoelastic parameter, c, may be extracted from an E-wave by fitting the velocity contour to the velocity of a damped harmonic oscillator, as described below. One manifestation of the relaxation/viscoelastic effects is the often observed (but always neglected) inflection point of the deceleration portion of the E-wave contour. Importantly, a triangular approximation to the E-wave, or a stiffness only model does not contain an inflection point in the contour. On the other hand, a stiffness and relaxation model of E-wave and A-wave filling ensures the presence of an inflection point through the existence of the additional relaxation parameter, c. E-waves with long concave up deceleration portions have high c values, while E-waves that closely approximate symmetric sine waves have low c values. Previous work in animals and humans has shown that the relaxation/viscoelasticity parameter, c, differentiates diabetic hearts from otherwise well-matched controls.

The delayed relaxation pattern is a discontinuous measure, although the progression of diastolic dysfunction is surely a continuous process. While the PRR clearly differentiates between groups with and without the delayed relaxation pattern, it is important to consider the physiological meaning of the PRR beyond its ability to differentiate. Indeed, as viscoelastic effects become more pronounced during filling, LV pressure will show a smaller recovery from minimum to diastasis compared to the initial pressure drop from MVO to minimum pressure. Thus, the PRR will decrease from an idealized value of 1 and approach a minimum value of 0 as energy losses associated with filling become more prominent.

An additional, thermodynamics based noninvasive, dimensionless index that involves chamber viscoelasticity, has been recently proposed. The kinematic filling efficiency index (KFEI) is the ratio of the actual, suction initiated E-wave volume normalized to the ideal volume achieved when suction initiated filling proceeds in a kinematically idealized and lossless (i.e., no energy loss, c=0) setting. Accordingly, KFEI decreases as relaxation/viscoelastic effects increase.

In regards to LV relaxation/viscoelasticity parameters during early filling, noninvasive indexes abound but clinically relevant invasive indexes do not exist. This problem is further compounded by the fact that $\tau$ does not fully capture relaxation effects nor does it strongly correlate to early-filling noninvasive indexes of relaxation/viscosity.

In an embodiment, a left ventricular pressure recovery ratio (PRR) is obtained during cardiac catheterization. It is invasively acquired, using in-vivo left ventricular pressure data. In an embodiment, the ventricular pressure data is time-variant, and the acquired data comprises discrete values sampled over time. PRR is an index of ventricular relaxation/viscoelasticity and is defined as the ratio of pressure differences between minimum and diastatic left ventricular pressure (LVP) to the difference between mitral valve opening (MVO) and minimum LV pressure. PRR extends the invasive determination of chamber relaxation properties using pressure information beyond $\tau$ to include the pressure of the left ventricle during filling, whereas $\tau$ measurement, by definition, stops when MVO occurs. The pressure values are obtained in real time and inserted into the ratio. The output is dimensionless, meaning that results may be compared between subjects and in one subject over time, if the cardiac catheterization is repeated in the same person at a future date.

PRR is a hemodynamic relaxation/viscoelasticity index for measuring the relaxation of the heart during early-rapid filling. PRR has been correlated to simultaneously acquired Doppler E-wave derived relaxation/viscoelasticity parameter with a correlation of $R^2$=0.78. The data has been supported by both high-sensitivity research grade catheters and fluid-filled disposable catheters used in the clinical setting.

While some methods for optimum hemodynamic assessment involve the use of high fidelity research grade electronic catheters, in the day-to-day clinical setting disposable catheters are employed, with which ventricular pressure is measured via a fluid column resident in a lumen of the catheter connected to a pressure transducer of the catheterization laboratory's hemodynamic recording equipment. The calculation of PRR is not dependent on the type of catheter used, although the fidelity of the LVP data obtained by a catheter with a fluid-filled lumen is not as high as an electronic catheter. Despite such technical differences regarding catheter, fluid-filled catheter derived PRR values do not significantly differ from high fidelity Millar catheter derived PRR values. In an embodiment, a comparison in eleven subjects between Millar catheter derived PRR values and fluid-filled catheter derived PRR values found an expected and very strong ($R^2$=0.75) linear correlation.

The clinical information provided by PRR regarding ventricular chamber properties from an invasive catheterization may be compared to the information provided by Doppler-echocardiography, adding additional information of use to a clinician performing the invasive procedure or serving as independent corroborative data for Doppler-derived assessment of left ventricular function. Because neither echocardiography nor catheterization is entirely sensitive and specific for any abnormality, PRR is a source of additional and independent information for patients undergoing a catheterization procedure, and in whom the hemodynamic data is available.

PRR has the advantage of being simple to calculate as well as having the potential to unify relaxation/viscoelasticity properties before and after mitral valve opening. Indeed, while τ fails to capture the more delayed relaxation property evident in the second patient from FIG. 4, the PRR in the second patient is significantly lower than the PRR in the first patient. This finding is in perfect agreement with the higher noninvasive relaxation/viscoelasticity parameter, c, values extracted from the second patient's E-waves, as well as the observed delayed relaxation pattern in the second patient.

PRR may also be understood from an energetic perspective. Elastic potential energy, stored in extracellular and intracellular elastic elements during the previous systole, manifests itself as an atrioventricular pressure gradient that drives flow. As blood velocity increases, the pressure gradient drops, and as blood velocity decelerates the pressure gradient reverses sign. If viscous energy losses are ignored, then the reversal gradient will be as strong as the initial pressure gradient, and if the energy losses are not ignored, then the reversal gradient will be somewhat damped out relative to the initial pressure gradient. Thus, a ratio of the peak pressure gradient driving flow to the peak reverse pressure gradient opposing flow will reflect relaxation/viscoelastic energy losses, and because of the relative symmetry between atrial pressure waveforms and LVP waveforms, the pressure gradient ratio that reflects energy losses can be approximated from the left ventricular pressure contour alone as the PRR. Thus the PRR reflects a balance between the fluid energy lost during filling and the initial stored elastic energy that drives blood flow.

An assumption that MVO pressure equals LVEDP has limitations. Although it has been shown that this is true in most normal cases, there could be exceptions. However, an analysis of 363 heart beats in 41 subjects, all of whom had normal mitral valves, and most of whom (39 of 41) had normal LVEF, is likely to minimize any systematic difference between MVO pressure and LVEDP.

The existence of mechanical suction initiated transmittal flow at MVO and the laws of fluid mechanics require that an intraventricular pressure gradient exists in all ventricles during early rapid filling. The exact location of the pressure sensor in the LV is variable from subject to subject and samples LVP at slightly different locations. Although this can generate some nonuniformity among subjects in the pressure measurement the generous number of patients studied and the large number of beats analyzed is likely to minimize this effect.

The relationship between PRR and KFEI was done for the 355 out of 363 underdamped E-waves ($4k-c^2>0$). The derivation between PRR and c was also in the underdamped regime. For simplicity, the 8 overdamped E-waves were not included in the KFEI calculation or the derivation.

In an ideal physiology experiment stiffness and relaxation would be experimentally varied by pharmacologic means or by volume infusion. Those methods were not a component of a Human Studies approved method of physiologic data acquisition. Rather, one should rely on physiologic respiration related and post PVC-related beat-to-beat variation of volume as a convenient experimental perturbation by which stiffness and relaxation/viscoelasticity chamber parameters in individual subjects were observed to vary. This has obvious limitations relative to ideal experiments, but it has the overwhelming advantage of utilizing in-vivo data, so its relevance to human, in-vivo physiology and clinical applicability is unquestionable.

Because two chambers having indistinguishable values for τ, LVEF, and catheterization determined chamber stiffness ($\Delta P/\Delta V$) may have substantially different values for E-wave determined deceleration times (DT), reliance on τ and $\Delta P/\Delta V$ provides an incomplete characterization of diastolic function. In fact, τ may be indistinguishable between two subjects where one subject has a DR pattern on echocardiography and the other has a normal transmitral pattern. Thus, a novel index that connects more directly than τ to filled-related relaxation properties is desirable. In the setting of a normal mitral valve, the dimensionless pressure recovery ratio (PRR), defined by the ratio of pressure difference between minimum and diastatic LVP to the difference between MVO and minimum LVP, carries information about chamber relaxation/viscoelasticity during early rapid-filling. The more relaxed and less viscoelastic the process, the more the pressure can recover from $LVP_{min}$ back toward MVO pressure. The establishment and validation of the causal connection between PRR and the E-wave derived index, c, advances the invasive characterization of diastolic function beyond isovolumic relaxation into early-rapid filling, and provides mechanistic insight into the relation between chamber properties and transmitral flow.

In contrast to clinical hemodynamic measurements, in current clinical echocardiography there is a noninvasive index related to LV relaxation/viscoelasticity that extends beyond isovolumic relaxation. This index is the E-wave deceleration time (DT) and when an E-wave has both a prolonged DT (DT>220 milliseconds) and a peak velocity lower than the A-wave peak velocity, the transmitral flow contour is said to possess the delayed relaxation pattern. Importantly, DT was originally interpreted as reflecting stiffness but recent work has shown that DT, especially when prolonged, is more accurately determined (in a mathematically precise way) jointly by chamber stiffness and by relaxation/viscoelasticity. It may seem natural, because both DT and τ are related to relaxation, to extend the interpretation of τ beyond isovolumic relaxation by assuming that τ serves as the hemodynamic analogue to DT. The assumption that τ and DT are closely concordant fails, however, as evidenced by FIG. 4, where two subjects having a similar ejection fraction and τ have highly discordant values for DT. The corresponding data are shown in Table 1. It is also important to note that the clinical finding of a delayed relaxation pattern observed in the subject shown in the right panel of FIG. 4 is often assumed to be related to a prolonged τ value. This assumed connection reflects the fact that the delayed relaxation pattern is a well-established finding indicative of diastolic dysfunction. However, the τ value in these two subjects is indistinguishable. FIG. 4 thus provides evidence for the causal disconnect between (invasive) τ and (non-invasive) DT and presence of or absence of delayed relaxation pattern, and serves to further support the search for a hemodynamic analogue to the relaxation/viscoelastic component of DT. The values shown in Table 1 are mean values plus or minus a standard deviation, τ is an isovolumic relaxation time constant, $\Delta P/\Delta V_{AVG}$ is an invasively measured average chamber stiffness, EF is an ejection fraction measured by ventriculography, HR is a heart rate, DT is a deceleration time, LVEDP is a left ventricular end diastolic pressure, PRR is a pressure recovery ratio, KFEI is a kinematic filling efficiency index, NS means not significant, and N.A. means not applicable.

TABLE 1

|  | Subject 1 | Subject 2 | Significance |
|---|---|---|---|
| Analyzed Heart Beats | 8 | 6 | N.A. |
| Tau ($\tau$) (ms) | 53 ± 3 | 52 ± 3 | N.S. |
| $(\Delta P/\Delta V)_{AVG}$ (mmHg/ml) | 0.10 ± 0.02 | 0.09 ± 0.02 | N.S. |
| EF (%) | 80 | 73 | N.A. |
| HR (bpm) | 57 ± 2 | 54 ± 1 | <0.05 |
| DT (ms) | 208 ± 20 | 261 ± 32 | <0.01 |
| E/A | 1.1 ± 0.1 | 0.8 ± 0.1 | <0.001 |
| LVEDP (mmHg) | 22 ± 2 | 17 ± 3 | <0.01 |
| PRR | 0.40 ± 0.10 | 0.21 ± 0.07 | <0.01 |
| PDF parameter c (1/s) | 20.0 ± 2.1 | 24.9 ± 2.1 | <0.01 |

Motivated by kinematic modeling of filling, the pressure recovery ratio (PRR) is a hemodynamic analogue of chamber relaxation/viscoelasticity beyond isovolumic relaxation. PRR, a dimensionless parameter defined by the ratio of the difference between diastasis and minimum LV pressures to the difference between mitral valve opening and minimum LV pressures, provides an easily determined lumped diastolic relaxation/viscoelastic parameter. In an embodiment, the high-fidelity Millar catheter measured PRR is compared with relaxation/viscoelasticity parameters extracted from simultaneously acquired Doppler transmitral flow E-waves. The calculation of PRR is shown as Equation 1:

$$PRR = (P_{Diastasis} - P_{min})/(P_{MVO} - P_{min}) \quad \text{Eq. (1)}$$

In accordance with mechanical suction-initiated ($\Delta P/\Delta V < 0$ at mitral valve opening) kinematic filling and energy conservation, in a purely elastic ventricle with negligible energy losses, the LVP contour will take the shape of an inverted symmetric sine wave between mitral valve opening (MVO) and E-wave termination (i.e., diastasis). A chamber with significant viscous energy losses or incomplete relaxation during filling, however, will have a pressure contour that recovers from minimum pressure ($P_{MIN}$) to a diastasis pressure ($P_{Diastasis}$) that is well below $P_{MVO}$. Thus, a quantitative estimate of relaxation/viscoelastic effects during early rapid filling may be made by normalizing the post-minimum pressure recovery during early-filling relative to the pressure drop between MVO pressure and $LVP_{min}$. $P_{MVO}$ is rarely measured in the clinical setting, however, and therefore a fiducial filling related pressure that is analogous to $P_{MVO}$ must be utilized in order to allow for routine clinical application of the PRR. There are several fiducial pressures that one may choose, and for subjects in normal sinus rhythm (NSR) the left ventricular end-diastolic pressure (LVEDP) is chosen to be a fiducial surrogate for $P_{MVO}$. This choice is supported by several studies showing that LVEDP is a reasonable approximation for $P_{MVO}$ in subjects with NSR and no significant pathophysiology. Thus, in NSR subjects, the pressure recovery ratio (PRR) is defined by Equation 2 as:

$$PRR = \frac{P_{Diastatic} - P_{min}}{P_{MVO} - P_{min}} = \frac{P_{Diastatic} - P_{min}}{LVEDP - P_{min}} \quad \text{Eq. (2)}$$

LVEDP cannot be used as the fiducial pressure for PMVO in the setting of atrial fibrillation (AF). In atrial fibrillation, the mitral valve opening pressure is different from LVEDP, which is the same as diastatic pressure. Without the estimation of mitral valve opening pressure, the original equation to calculate PRR is not applicable. Instead, LV pressure at minimum dP/dt ($P_{dP/dtMin}$) is used as the fiducial early-rapid filling related pressure in the setting of AF. This fiducial pressure is the pressure when the pressure drops the fastest during the isovolumic relaxation portion before the mitral valve opens for the same diastole. This time point can be found by looking at the time derivative of the pressure data. Thus PRR in AF subjects is defined as shown in Equation (3):

$$PRR^{(AFib)} = \frac{P_{Diastatic} - P_{Min}}{P_{dP/dt_{Min}} - P_{Min}} \quad \text{Eq. (3)}$$

This $PRR^{(AFib)}$ index may be used in atrial fibrillation patients when no mitral valve opening pressure is available. It is not limited to atrial fibrillation patients. Other fiducial pressures may also be chosen to calculate the pressure recovery ratio.

For example, the fiducial pressure may be estimated by considering the duration of diastole. Starting with the end diastolic pressure, found from the R-wave peak, the duration of diastole may be subtracted, leaving the time at mitral valve opening, which is the very fiducial marker being sought. Fortunately there is a strong correlation between heart rate and mechanical duration of diastole (MDD), which is the time between the onset of echocardiographic E-wave and the end of the echocardiographic A-wave. In order to do this, first, the time between the ECG R-wave of the beat being measured and the previous ECG R-wave is measured. This time interval is called RR interval. From the RR interval and the published relationship between RR interval and MDD time, the MDD time is calculated as shown below in Equation (24). The MDD time is subtracted from the time at end diastole marked in A-fib by the ECG R-wave to obtain the time of the onset of filling or estimated mitral valve opening time. The pressure at this time point is then taken to be the estimated mitral valve opening pressure ($P_{MVO\_est}$), or the fiducial pressure value.

Datasets from 41 subjects with NSR and 9 subjects with atrial fibrillation (AF) (total of 50 subjects) were selected from the Cardiovascular Biophysics Laboratory Database of simultaneous micromanometric catheter recorded left ventricular pressure (LVP) and echocardiographic data. Subjects were scheduled for elective diagnostic cardiac catheterization to rule out the presence of coronary artery disease. All subjects provided informed consent prior to the procedure in accordance with a protocol approved by the Barnes-Jewish Hospital/Washington University Human Research Protection Office (HRPO). The criteria for data selection included: normal valvular function, no active ischemia, and no significant merging between echocardiographic E-waves and A-waves. None of the 50 subjects had previous myocardial infarction or peripheral vascular disease. Thirty nine out of forty one NSR subjects had normal EF and 4 out of 9 AF subjects had an ejection fraction (EF) lower than 55%.

Particular care was taken to include subjects with premature ventricular contraction (PVC) during data acquisition in the analysis. Filling beats following PVCs are known to reflect worsened relaxation with load change, and therefore offer a novel in-vivo physiological test of the PRR. Among the twenty three subjects in this study, nine subjects had good quality echocardiographic data when PVC occurred during the data acquisition.

Figure 5:
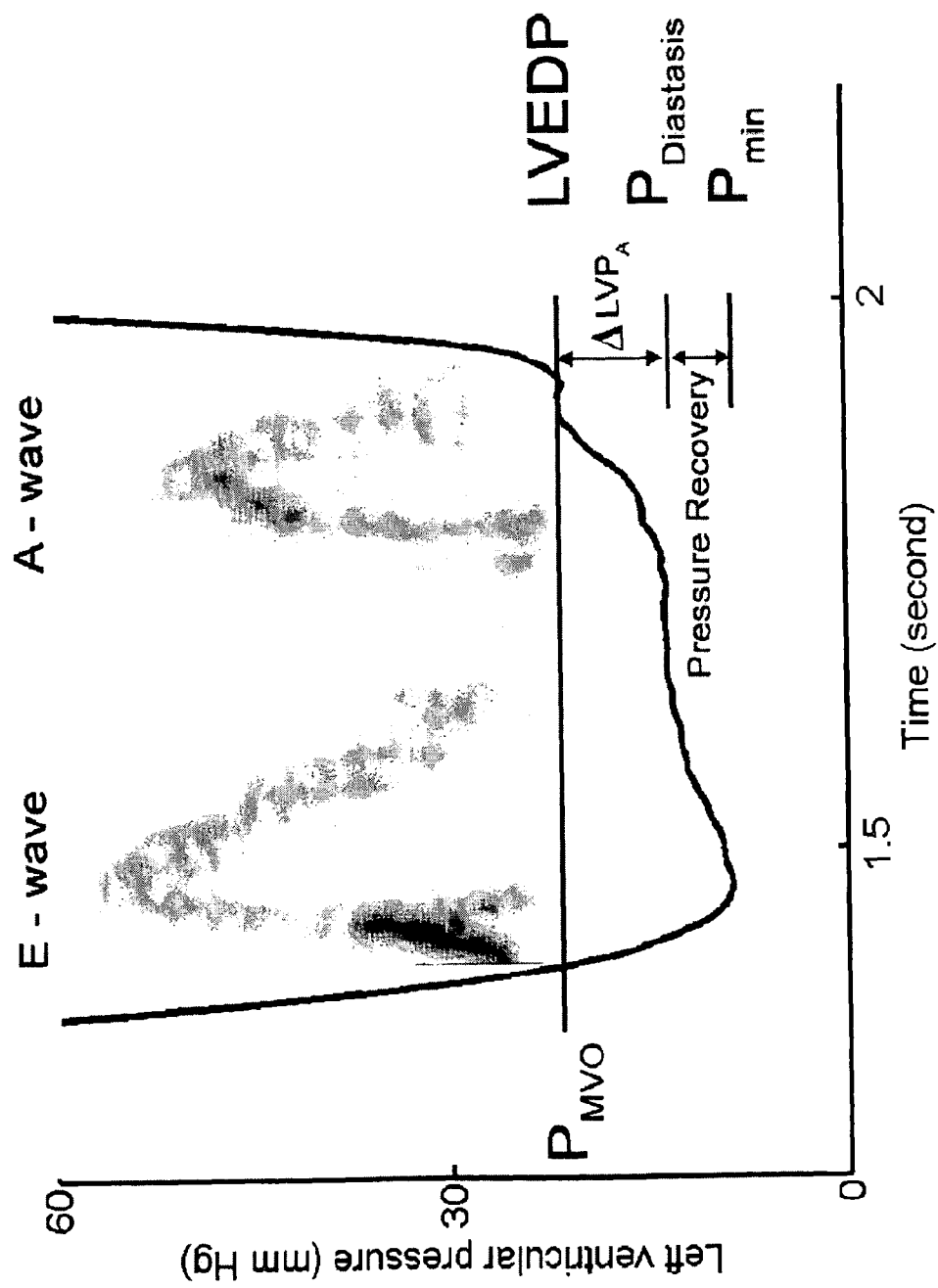
FIG. 5 is a graph showing an exemplary diastolic LVP contour with simultaneous transmitral flow.

The method of simultaneous high fidelity, in-vivo pressure-volume and echocardiographic transmitral flow data recording has been previously detailed. High fidelity pressure and noninvasive Doppler transmitral flow data were synchronized and analyzed offline using custom analysis software. A typical LVP tracing during diastole with simultaneous mitral E-waves and A-waves is shown in FIG. 5. As such, FIG. 5 shows an echocardiographic E-wave and A-wave, pressure recovery, $\Delta LVP_A$, $P_{Diastasis}$, $P_{min}$, LVEDP, $P_{MVO}$.

Subjects in NSR were divided into three groups related to presence or absence of an echocardiographically determined delayed relaxation pattern. Group 1, the full delayed relaxation pattern group (DR), consisted of subjects with both an E/A<1 and a DT>220 ms. Group 2, the partially delayed relaxation group (PDR), consisted of subjects with either an E/A<1, or a DT>220 ms. Group 3, the normal relaxation pattern group (NML) consisted of subjects with transmittal flow patterns where E/A>1 and DT<220 ms. Table 1 above presents demographic data for the enrolled NSR and AF subjects. Several hemodynamic variables, including the novel PRR index, and several echocardiographic variables were analyzed from multiple beats in each subject.

For each subject, an average of 10 beats were analyzed (363 heart beats total for 41 NSR subjects, 113 heart beats for 9 AF patients, total of 476 heart beats). Conventional, triangle approximations of E-wave and A-wave shapes provided peak E-wave velocity ($E_{peak}$), E-wave acceleration and deceleration times (AT and DT), E-wave duration and velocity-time integral ($E_{dur}$ and $VTI_E$), peak A-wave velocity ($A_{peak}$), and A-wave velocity-time integral ($VTI_A$). Furthermore the ratio of $E_{peak}$ to $A_{peak}$ ($E_{peak}/A_{peak}$) and $VTI_E$ to $VTI_A$ ($VTI_E/VTI_A$), was also calculated for all beats.

In addition, all E-waves were subjected to Parametrized Diastolic Filling (PDF) model-based image processing (MBIP) to yield E-wave specific kinematic parameters (relaxation/viscoelasticity parameter c, stiffness parameter k, initial load parameter $x_o$). Thus individual k, c, and $x_o$ (the PDF parameters) parameters were determined for each analyzed E-wave. Each PDF parameter serves to mathematically determine the E-wave contour, and has been shown to have specific physiological analogues. The c parameter is particularly relevant to filling-related relaxation because as an E-wave's c parameter increases, the wave becomes less tall and longer, which is consistent with the delayed relaxation pattern. The c parameter has previously been shown to be related to the relaxation/viscoelastic component of the E-wave DT, but conceptually may be considered to be a continuous measure of the degree of delayed relaxation that a particular E-wave possesses. The MBIP method by which PDF parameters are obtained from digitized recordings of transmitral flow has been previously described and validated. Furthermore, the dimensionless, kinematic filling efficiency index (KFEI), which is the E-wave filling volume normalized to an idealized lossless filling volume, was also computed for all underdamped E-waves ($4k-c^2>0$).

Hemodynamic parameters ($P_{Min}$, $P_{dP/dtMin}$, $P_{Diastasis}$, LVEDP, $\tau$) were determined from the high-fidelity Millar LVP data for each beat. Diastatic pressure and LVEDP values were measured at the peaks of the P-wave and R-wave on the simultaneous ECG, respectively using a custom LABVIEW® (LABVIEW is a registered trademark of National Instruments, Austin, Tex.) program. Isovolumic relaxation time constant ($\tau$) was calculated from the isovolumic pressure decay contour for all measured beats in each patient according to conventional methods. The PRR was calculated according to Equation 3 for each beat in each NSR subject, and according to Equation 4 for each beat in each AF subject.

The sensitivity of the PRR concept to the given choice of fiducial $P_{MVO}$ pressure was further analyzed. Instead of choosing LVEDP as the fiducial filling pressure, 11 additional choices of fiducial pressures were considered. Four PRR definitions ($PRR^1$, $PRR^2$, $PRR^3$, $PRR^4$) were considered where the fiducial pressure was chosen 0 ms, 10 ms, 30 ms, and 60 ms after $P_{Max}$, respectively. In additional 7 additional PRR definitions ($PRR^{5-11}$) were considered where the fiducial pressure was chosen −20 ms, −10 ms, −5 ms, 0 ms, 10 ms, 20 ms, and 30 ms after the minimum dP/dt, respectively. See FIG. 2A for a representation of these alternative fiducial pressure values. PRR values defined by the 11 alternative fiducial pressure choices described above were calculated for all beats in all NSR subjects.

In the two representative subjects in FIG. 4, the invasive average chamber stiffness ($\Delta P/\Delta V)_{AVG}$ and early rapid filling chamber stiffness ($\Delta P/\Delta V)_E$ were calculated as previously described. Briefly, the averaged chamber stiffness (($\Delta P/\Delta V)_{AVG}$) was calculated as the ratio of the change in pressure to the change in volume during the time interval from minimum LVP to end diastole using Equation (4):

$$(\Delta P/\Delta V)_{AVG} = \frac{LVP_{End\_diastolic} - P_{min}}{V_{End\_diastolic} - V_{LVP(min)}} \qquad \text{Eq. (4)}$$

Early rapid filling stiffness ($\Delta P/\Delta V)_E$ was calculated as the ratio of the change in pressure to the change in volume during the time interval from minimum LVP to diastasis, using Equation (5):

$$(\Delta P/\Delta V)_E = \frac{LVP_{Diastatic} - P_{min}}{V_{Diastatic} - V_{LVP(min)}} \qquad \text{Eq. (5)}$$

Volume changes were calculated by multiplying the relevant E-wave and A-wave velocity time integral by an average effective mitral valve area of approximately 5.0 cm$^2$, as reported in several studies.

All invasive and noninvasive parameters of interest (E/A, $VTI_E/VTI_A$, $VTI_E/(VTI_E+VTI_A)$, DT, PRR, c, $\tau$) were averaged for each of the 50 subjects and several comparisons were performed. First, values of interest were compared between Group 1 (DR), Group 2 (PDR), and Group 3 (NML) subjects. Student t-tests were utilized to assess whether the PRR, defined by Equation (3) or by one of the alternate fiducial pressures ($PRR^{1-11}$), was significantly different between groups. Similar analysis was performed for DT, E/A, and $\tau$, and LVEDP. Secondly, values of interest were compared in a continuous fashion through linear regressions. Linear regressions between c, DT, E/A, $VTI_E/VTI_A$, and PRR were performed. For each variable of interest, two types of linear regressions were calculated. First, linear regressions between each variable of interest and PRR for all 363 beats pooled from all NSR subjects were performed. Second, linear regression of the variables averaged over each of the 41 NSR subjects was also performed relative to a similarly averaged PRR value. Equivalent analysis was undertaken for the 9 subjects with AF. In addition, 11 separate linear regressions between c and the $PRR^{1-11}$ values defined by each of the alternative fiducial pressure choices were performed. All statistical analyses utilized MS-Excel® (Excel is a registered trademark of Microsoft Corp., Redmond, Wash.).

The clinical descriptors of the forty one NSR and nine AF subjects and their hemodynamic and echocardiographic indexes are shown in Table 2. In Table 2, * indicates significantly different from DR group; † indicates significantly different from PDR group; ‡ indicates LVEDP=$P_{Diastasis}$ in AF; ** indicates that PRR is defined by Equation (4); DR indicates the delayed relaxation pattern group; PDR indicates the partial delayed relaxation pattern group; and NML indicates the normal group.

In addition, NSR indicates the normal sinus rhythm group including all patients in DR, PDR, and NML groups; AF indicates atrial fibrillation; VTI indicates velocity time integral; LVEF is the left ventricular ejection fraction; LVEDV is the left ventricular end-diastolic volume; LVEDP is the left ventricular end-diastolic pressure; E/A is the ratio of $E_{peak}$ and $A_{peak}$; and LVEF is determined by ventriculography.

For the rest of the twenty one subjects, post PVC beats which had curved phase plane segments were excluded. For the beats which had nearly linear isovolumic pressure decay segments in the pressure phase plane (n=355), in which case τ could be obtained by fitting the segment with a straight line

TABLE 2

|  | DR | PDR | NML | NSR | AF |
|---|---|---|---|---|---|
| Size of the group | 9 | 15 | 17 | 41 | 9 |
| Age | 65 ± 7 | 60 ± 9 | 52 ± 7*† | 58 ± 9 | 61 ± 9 |
| Sex (m/f) | 6/3 | 11/4 | 8/9 | 25/16 | 8/1 |
| Race (w/b) | 7/2 | 12/3 | 13/4 | 32/9 | 7/2 |
| HR | 61 ± 8 | 60 ± 7 | 64 ± 8 | 62 ± 8 | 84 ± 22 |
| EF (%) | 67 ± 11 | 71 ± 8 | 75 ± 7* | 72 ± 9 | 51 ± 19 |
| LVEDV (ml) | 180 ± 51 | 145 ± 32 | 146 ± 39 | 153 ± 42 | 170 ± 50 |
| $P_{Min}$ (mmHg) | 11 ± 3 | 8 ± 2* | 9 ± 3 | 9 ± 3 | 9 ± 3 |
| $P_{Diastasis}$ (mmHg) | 13 ± 4 | 12 ± 2 | 14 ± 4 | 13 ± 3 | 17 ± 6 |
| LVEDP (mmHg) | 20 ± 6 | 19 ± 3 | 19 ± 4 | 19 ± 4 | 17 ± 6 |
| PRR | 0.31 ± 0.12 | 0.39 ± 0.08* | 0.48 ± 0.08*† | 0.41 ± 0.11 | N.A.** |
| PDF relaxation parameter c (1/s) | 21.3 ± 2.5 | 19.2 ± 1.9* | 17.4 ± 1.7*† | 18.9 ± 2.4 | 17.6 ± 3.4 |
| PDF relaxation parameter k (1/s$^2$) | 169 ± 28 | 168 ± 45 | 174 ± 32 | 170.8 ± 35.8 | 241.2 ± 78.7 |
| Isovolumic relaxation time constant (τ) (ms) | 53 ± 5 | 52 ± 7 | 51 ± 6 | 52 ± 6 | 56 ± 6 |
| E-wave acceleration time (ms) | 98 ± 9 | 97 ± 16 | 92 ± 12 | 95 ± 13 | 95 ± 17 |
| E-wave deceleration time (ms) | 239 ± 15 | 225 ± 36 | 185 ± 27*† | 211 ± 36 | 187 ± 44 |
| E-wave duration (ms) | 336 ± 22 | 320 ± 49 | 278 ± 33*† | 306 ± 45 | 283 ± 60 |
| E-wave peak (cm/s) | 65.9 ± 15.2 | 76.3 ± 15.9 | 81.5 ± 15.3* | 76 ± 16 | 90 ± 35 |
| A-wave peak (cm/s) | 73.2 ± 12.0 | 71.8 ± 11.2 | 69.5 ± 14.4 | 71 ± 13 | N.A. |
| E/A | 0.9 ± 0.1 | 1.1 ± 0.2* | 1.2 ± 0.2* | 1.1 ± 0.2 | N.A. |
| E-wave VTI (cm) | 11.0 ± 2.2 | 12.3 ± 3.7 | 11.3 ± 2.7 | 12 ± 3 | 13 ± 7 |
| A-wave VTI (cm) | 6.9 ± 1.4 | 7.7 ± 1.2 | 6.1 ± 1.3† | 7 ± 1 | N.A. |
| $VTI_E/VTI_A$ | 1.6 ± 0.2 | 1.6 ± 0.3 | 1.9 ± 0.3*† | 1.7 ± 0.3 | N.A. |

In the DR group (n=9), 3 (33%) subjects had normal τ. In the PDR group (n=15), 9 (60%) subjects had normal τ. In the NML group (n=17), 8 (47%) subjects had normal τ. The τ values in the three groups do not differ from each other significantly (p>0.05) by an unpaired Student's t-test.

Two representative subjects from Group 1 and Group 3 respectively illustrating the discordance between delayed relaxation pattern and τ are shown in FIG. 4. Although the two subjects had similar τ, subject 1 had a normal filling pattern and subject 2 had a delayed relaxation pattern. Detailed data from these two subjects are given in Table 1. These results showed that delayed relaxation pattern observed in E-waves and A-waves do not correlate with prolonged τ.

As shown in Table 2, DT did not differentiate DR from PDR group, but did differentiate DR and PDR from NML (p<0.001, p<0.01, respectively). Duration of the E-wave differentiated DR and PDR from NML (p<0.001, p<0.01, respectively), but not DR from PDR group. The peak of E-wave velocity ($E_{peak}$) does not differentiate DR from PDR or PDR from NML, but does differentiate DR from NML (p<0.05). The peak of A-wave ($A_{peak}$) were similar in all three groups. However, E/A differentiated DR from PDR (p<0.05) and NML (p<0.001), but not PDR from NML. $VTI_E/VTI_A$ was different between PDR and NML group (p<0.01) and between DR and NML group (p<0.05), but similar between DR and PDR group (p>0.05). PDF parameter c was significantly different among the three groups (p<0.05 between DR and PDR, p<0.01 between PDR and NML, p<0.001 between DR and NML).

Figure 6:
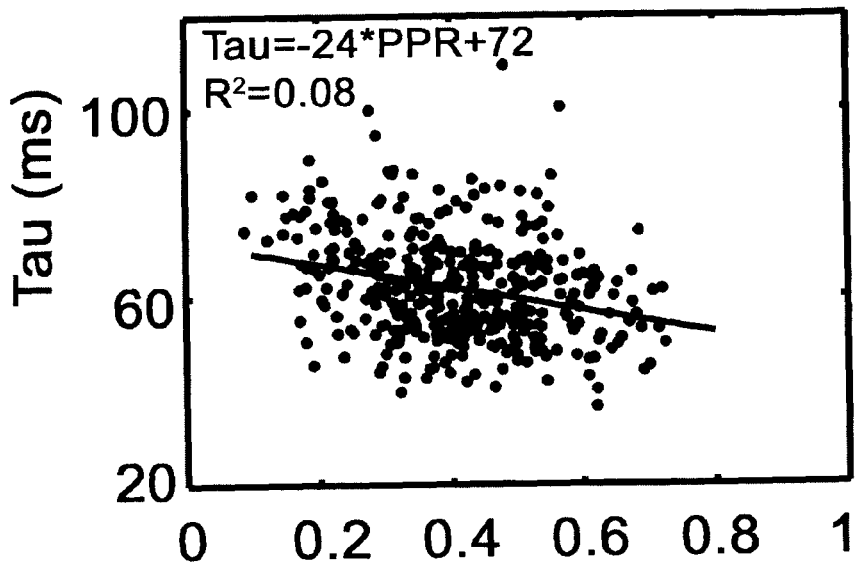
FIG. 6 is a graph showing an exemplary time constant of isovolumic relaxation ($\tau$) versus a pressure recovery ratio (PRR) for the pooled data of 41 subjects for all cardiac cycles with linear phase plane segments during IVR.
Figure 7:
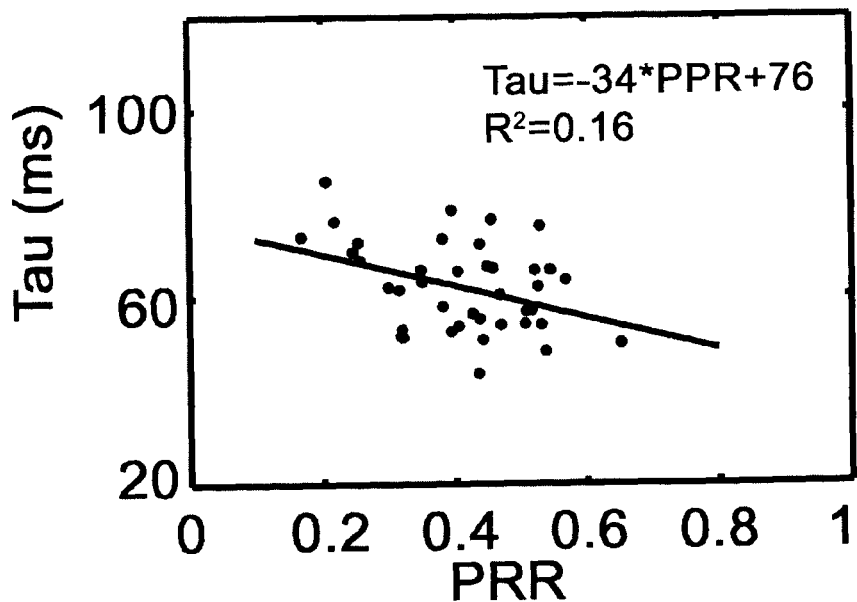
FIG. 7 is a graph showing an exemplary time constant of isovolumic relaxation ($\tau$) versus PRR for the averaged data of 41 subjects for all cardiac cycles with linear phase plane segments during IVR.

As expected, the relationship between echocardiographic DT is not significantly related to PRR over either all analyzed beats or averaged values for each subject (result not shown). For two out of forty one subjects, the IVR phase planes for all analyzed beats had curved isovolumic relaxation segments.

the isovolumic relaxation time constant (τ), τ was poorly related to PRR over all analyzed beats ($R^2$=0.08) and over averaged values for each subject ($R^2$=0.16), as shown in FIGS. 6 and 7.

Figure 8:
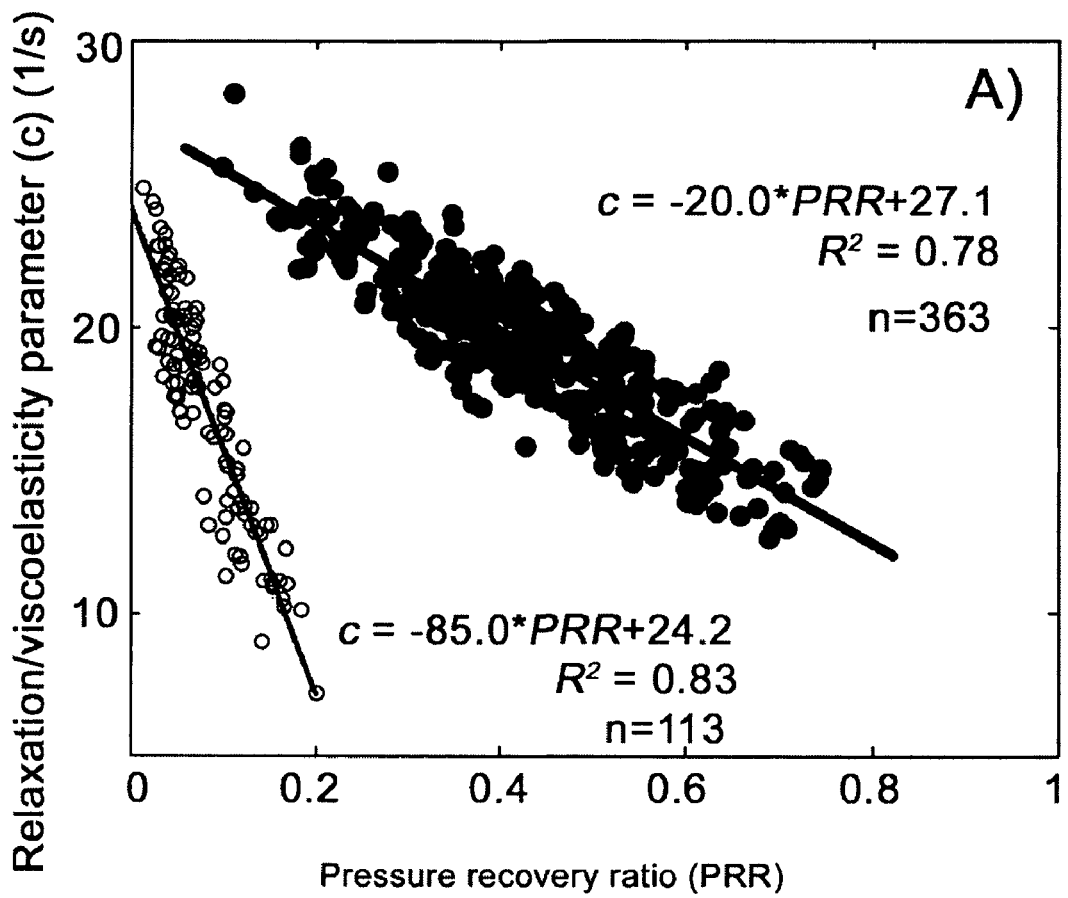
FIG. 8 is a graph showing an exemplary PRR versus the E-wave-derived relaxation/viscoelasticity parameter c in all 41 normal sinus rhythm (NSR) subjects (363 heart beats) and 9 atrial fibrillation (AF) subjects (113 heart beats).

As predicted by the algebraic derivation described below, PRR and c had a strong linear relationship (c=−20.0×PRR+ 27.1, $R^2$=0.78) over all analyzed beats, as shown in FIG. 8. When average values for each subject were compared, PRR and c maintained the expected strong linear correlation (c=− 19.6×PRR+26.9, $R^2$=0.79). Table 3 provides the linear regression of PRR vs. c for all individual subjects. PRR did not significantly correlate with typical noninvasive indexes of diastolic function such as E/A ($R^2$=0.12), $VTI_E/VTI_A$ ($R^2$=0.11), and DT ($R^2$=0.02) in all heart beats. PRR values were significantly different between the DR and PDR group (p<0.05), the PDR and NML group (p<0.01), and DR and NML group (p<0.001) (shown in Table 2).

TABLE 3

| Subject | Linear fit slope (1/s) | Linear fit intercept (1/s) | $R^2$ |
|---|---|---|---|
| 1 | −17.80 | 27.21 | 0.93 |
| 2 | −16.91 | 26.48 | 0.88 |
| 3 | −23.25 | 28.71 | 0.81 |
| 4 | −22.25 | 26.84 | 0.89 |
| 5 | −23.02 | 29.31 | 0.93 |
| 6 | −22.91 | 26.70 | 0.96 |
| 7 | −25.14 | 29.98 | 0.92 |
| 8 | −30.83 | 32.04 | 0.97 |
| 9 | −18.56 | 26.02 | 0.89 |
| 10 | −44.53 | 37.17 | 0.91 |
| 11 | −25.48 | 28.72 | 0.96 |
| 12 | −23.36 | 30.45 | 0.86 |
| 13 | −36.86 | 32.25 | 0.93 |
| 14 | −33.24 | 29.25 | 0.86 |

TABLE 3-continued

| Subject | Linear fit slope (1/s) | Linear fit intercept (1/s) | $R^2$ |
|---|---|---|---|
| 15 | −19.53 | 27.42 | 0.88 |
| 16 | −22.66 | 27.18 | 0.96 |
| 17 | −31.06 | 30.89 | 0.94 |
| 18 | −27.59 | 29.53 | 0.92 |
| 19 | −19.68 | 28.30 | 0.44 |
| 20 | −32.25 | 29.98 | 0.71 |
| 21 | −22.51 | 28.58 | 0.80 |
| 22 | −27.87 | 30.10 | 0.72 |
| 23 | −15.54 | 22.81 | 0.84 |
| 24 | −19.82 | 28.59 | 0.86 |
| 25 | −21.61 | 29.45 | 0.70 |
| 26 | −25.41 | 31.53 | 0.69 |
| 27 | −20.55 | 28.09 | 0.90 |
| 28 | −17.27 | 26.53 | 0.60 |
| 29 | −18.53 | 26.28 | 0.75 |
| 30 | −24.64 | 27.97 | 0.88 |
| 31 | −17.82 | 26.32 | 0.83 |
| 32 | −16.44 | 25.39 | 0.92 |
| 33 | −10.32 | 22.30 | 0.73 |
| 34 | −23.32 | 30.35 | 0.72 |
| 35 | −21.88 | 28.30 | 0.57 |
| 36 | −28.32 | 30.70 | 0.96 |
| 37 | −50.40 | 36.61 | 0.69 |
| 38 | −14.88 | 23.36 | 0.90 |
| 39 | −43.55 | 36.92 | 0.67 |
| 40 | −40.09 | 32.39 | 0.64 |
| 41 | −15.28 | 22.96 | 0.76 |

Among the 11 PRR defined by 11 different fiducial pressures ($PRR^{1-11}$), eight differentiate DR group from PDR group ($p<0.05$), and ten differentiate DR group from NML group ($p<0.05$).

If the pressure recovery from minimum pressure to diastatic pressure is not normalized relative to any fiducial pressure, the correlation between the magnitude of pressure recovery and c is still modest ($R^2=0.31$). Pressure recovery (mmHg) without normalization can differentiate DR from PDR group and DR from NML group ($p<0.05$).

The clinical descriptors of the nine AF subjects and their hemodynamic and echocardiographic indexes are shown in Table 2. Equation 3 defined PRR as strongly correlated ($R^2=0.83$) with c across the nine AF subjects (FIG. 8).

Fluid mechanics dictates that the PRR is related to energy loss and the relative efficiency of filling. Previous work has shown that the E-wave transmitral velocity contour may be modeled causally as the result of lumped tissue recoil and resistance forces. The energy loss in the model is accounted for by a damping parameter, called c. A ventricle with no energy loss during filling would have a symmetric E-wave with a c value of 0, whereas a ventricle with significant energy losses during filling would have a decreased E-wave peak, and a prolonged tail, and an elevated value of c. Therefore, a c value of zero theoretically corresponds to a PRR value of 1. While the strongest correlation between c and PRR predicts a c value of 7.08/s at a PRR value of 1 ($R^2=0.78$), one observes a slightly weaker correlation ($R^2=0.75$) if the regression is set to cross the PRR axis at PRR=1.

Thus the results of FIG. 8, where a strong linear relationship is observed between c and PRR, support the conclusion that PRR is simply an invasive analog for the E-wave determined damping parameter c. In other words, PRR provides a measure of the relaxation portion of the filling-related pressure contour, while c provides a measure of the relaxation portion of the E-wave.

Figure 9:
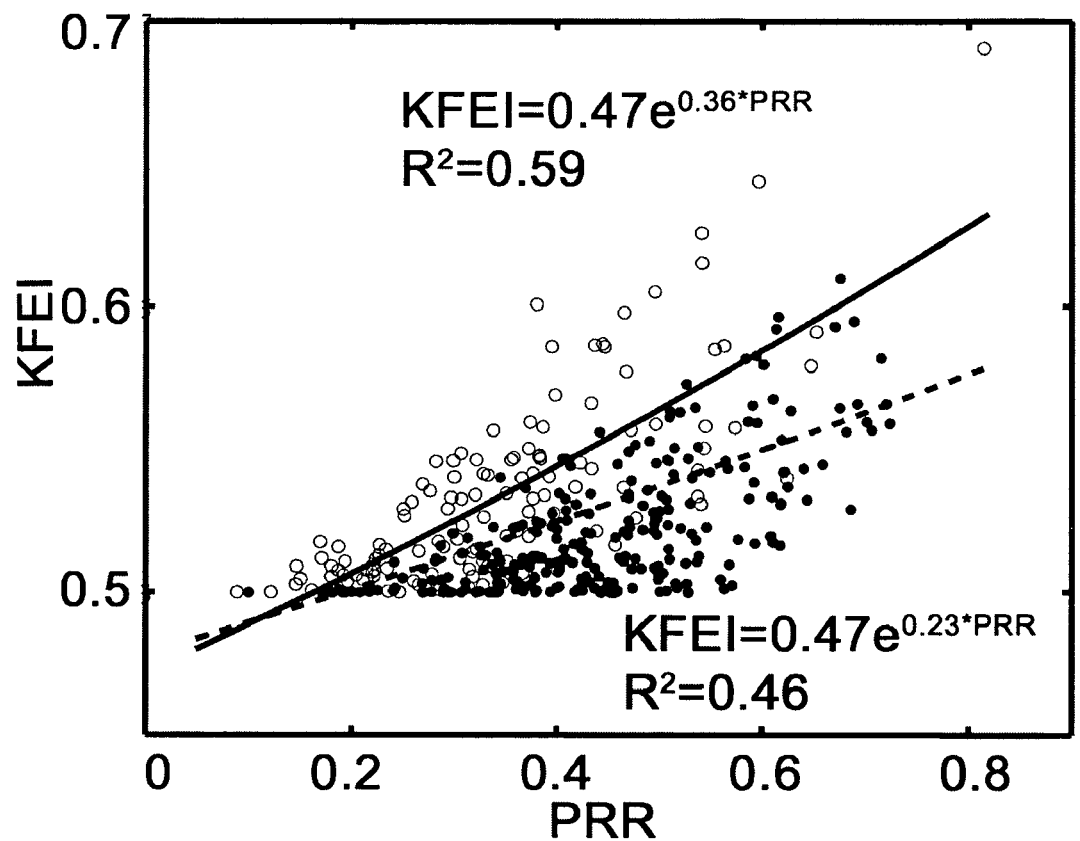
FIG. 9 is a graph showing an exemplary kinematic filling efficiency index (KFEI) versus PRR in two groups of subjects dichotomized according to E-wave-derived chamber stiffness parameter k.

In the 355 underdamped E-waves PRR was exponentially correlated with KFEI, a previously validated dimensionless index that characterizes the efficiency of diastolic filling in thermodynamic terms, as shown in FIG. 9. KFEI is a function of both k and c, while PRR is a function of only c. If the data are dichotomized by k (low k group, $k=149.4\pm30.0/s^2$, n=156; high k group, $k=227.0\pm56.7/s^2$, n=66), KFEI has a positive relationship with PRR in both groups ($R^2=0.47$ and 0.71, respectively).

In order to understand and explain the mechanisms by which two chambers having indistinguishable values for $\tau$, LVEF, and stiffness as shown in FIG. 4 may have distinguishable values for E-wave DT, new ideas for characterization of ventricular relaxation/viscoelasticity are required. To address this problem, PRR is used, which is an invasive, dimensionless index of ventricular relaxation/viscoelasticity. PRR utilizes post-isovolumic relaxation generated hemodynamic data, and in conjunction with $\tau$, is intended to provide a more complete picture of the relaxation/viscoelasticity components of diastolic function throughout diastole. To facilitate exposition, a first-principle based algebraic derivation is provided to detail the expected linear connection between the PRR and E-wave based relaxation/viscoelastic parameters. This linear correlation is tested using in-vivo hemodynamic-echocardiographic data obtained from twenty three subjects.

The PDF formalism models the kinematics of early, rapid LV filling in analogy to the motion of a damped simple harmonic oscillator (SHO). The governing equation of motion is:

$$m\frac{d^2x}{dt^2} + c\frac{dx}{dt} + kx = 0 \qquad \text{Eq. (6)}$$

The formalism solves the "inverse problem" by providing (mathematically) unique parameters c, k, and $x_o$ that determine each Doppler E-wave contour. The initial displacement of the oscillator $x_o$ (cm) is linearly related to the E-wave VTI (i.e., a measure of volumetric preload), chamber stiffness ($\Delta P/\Delta V$) is linearly related to the model's spring constant k ($g/s^2$) while the oscillator's damping constant or chamber viscoelasticity/relaxation index c (g/s) characterizes the resistance (relaxation/viscosity) and energy loss associated with filling. The contour of the clinical E-wave is predicted by the (underdamped) solution for the velocity of a damped oscillator, given by:

$$v(t) = -\frac{x_o k}{\omega}\exp(-\alpha t)\sin(\omega t) \qquad \text{Eq. (7)}$$

where $\alpha=c/2m$, and $\omega=\sqrt{4mk-c^2}/2m$. PDF parameter values for $x_o$, c, and k are determined using the Levenberg-Marquardt algorithm fit to the maximum velocity envelope via a custom LABVIEW® interface. By setting m=1, the parameters per unit mass may be calculated. Some additional PDF-derived indexes include the stored elastic strain energy available for driving ventricular suction ($\frac{1}{2}kx_o^2$) and the peak atrio-ventricular pressure gradient ($kx_o$).

Using the PDF formalism, a dimensionless kinematic filling efficiency index (KFEI) has been derived and validated. This dimensionless index is the ratio of the filling volume of an actual, clinical E-wave relative to ideal, zero energy loss (c=0) filling volume for the same E-wave determined by the same oscillator parameters (k and $x_o$). Using PDF formalism notation, KFEI is given by:

$$KFEI = \frac{1 + e^{-\frac{c}{2} \times Edur}}{2}$$

$$= \frac{1 + e^{\frac{c\pi}{\sqrt{4k-c^2}}}}{2}$$

Eq. (8)

for E-waves whose contours are well fit by underdamped kinematics ($4k-c^2>0$) (355 out of 363 heart beats in the study). KFEI has been shown to be lower in diabetic subjects compared with normal controls.

The relation between PRR and the PDF parameter c may be derived from Bernoulli's equation for non-steady flow using Equation (9):

$$LAP = LVP + \frac{1}{2}\rho v^2 + \rho \int_{LA}^{LV} \frac{\partial v(s,t)}{\partial s} ds$$

Eq. (9)

where it is assumed that blood flow velocity in the atrium is small compared with the blood flow velocity in the ventricle. In Equation (9), $\rho$ is the density of blood, v the transmitral velocity and is a function of both location along the streamline and time, LAP is the left atrial pressure, and LVP is the left ventricular pressure. The integral is the acceleration term, and may be rewritten as M(dv/dt), where M (constant) is the mitral inertiance. Equation (9) may thus be expressed as shown by Equation (10):

$$LAP = LVP + \frac{1}{2}\rho v^2 + M\frac{dv}{dt}$$

Eq. (10)

where the atrio-ventricular pressure gradient $\Delta P$ is shown by Equation (11):

$$\Delta P = LAP - LVP = \frac{1}{2}\rho v^2 + M\frac{dv}{dt}$$

Eq. (11)

It is well established that both LVP and LAP decrease and then recover during early filling, eventually both reaching the same diastatic pressure. Thus, while in final form PRR is defined in terms of the LVP, one could easily justify defining a similar pressure recovery ratio in terms of LAP, or in terms of the pressure gradient $\Delta P$. Indeed, the pressure gradient reaches maximum shortly after mitral valve opening and reaches a negative peak towards the end of early filling when transmitral flow is decelerating. Thus, for ease of derivation, the peak pressure gradient ratio (PPGR) is defined as:

$$PPGR = \left|\frac{\Delta P_{PeakPositiveGradient}}{\Delta P_{PeakNegativeGradient}}\right|$$

Eq. (12)

PPGR may serve as a reasonable surrogate for the PRR defined using LVP measurements. This assumption is reasonable because of the relative symmetry between LVP and LAP signals. It is important to note that this simplification allows for a clear derivation, but would not be useful clinically because LAP is not routinely measured in the catheterization lab. Thus, for clinical purposes the PRR derived from LVP is ideal.

Before Equation (12) may be evaluated exactly, several further simplifications in the Bernoulli expression may be made. According to PDF formalism, the transmitral blood flow velocity contour is accurately predicted by simple harmonic oscillatory motion (Equation (7)). The velocity of the E-wave (per unit mass) is rewritten in Equation (13):

$$v(t) = -\frac{x_o k}{\omega}\exp(-ct/2)\sin(\omega t)$$

Eq. (13)

in the underdamped regime ($4k>c^2$) (accounts for 355 out of 363 beats in the study). The derivative of velocity is acceleration and is:

$$\dot{v}(t) = -\frac{x_o k}{\omega}\left(\omega\exp(-ct/2)\cos(\omega t) - \frac{c}{2}\exp(-ct/2)\sin(\omega t)\right)$$

Eq. (14)

Thus Equation (12) and Equation (13) may be used to expand Equation (14).

From Equation (7), LVP and LAP crossover (LAP=LVP, or $\int v(t)=0$) occurs at t=DT starting from the onset of E-wave, and $$DT = \frac{\pi}{\omega} - \frac{1}{\omega}a\tan\left(\frac{\omega}{\alpha}\right)$$

Eq. (15)

$$AT = \frac{1}{\omega}a\tan\left(\frac{\omega}{\alpha}\right)$$

Eq. (16)

where AT is acceleration time. At time t=DT, $$LAP - LVP = 0 = \frac{1}{2}\rho v^2\bigg|_{DT} + M\frac{dv}{dt}\bigg|_{DT}$$

Eq. (17)

Thus, the mitral inertiance factor may be solved for and internal consistency of equations ensured.

$$M = -\frac{(1/2)\rho v^2|_{DT}}{\dot{v}|_{DT}} = \frac{1}{2}\rho x_o\left(\frac{\sqrt{k}}{c}\right)e^{(-cDT/2)}$$

Eq. (18)

Hence the pressure gradient at any given time t is:

$$\Delta P(t) = LAP(t) - LVP(t)$$

$$= \frac{1}{2}\rho v(t)^2 + M\frac{dv(t)}{dt}$$

$$= \frac{1}{2}\rho\left[v(t)^2 + x_0\frac{\sqrt{k}}{c}e^{(-cDT/2)}\dot{v}(t)\right]$$

Eq. (19)

Figure 10:
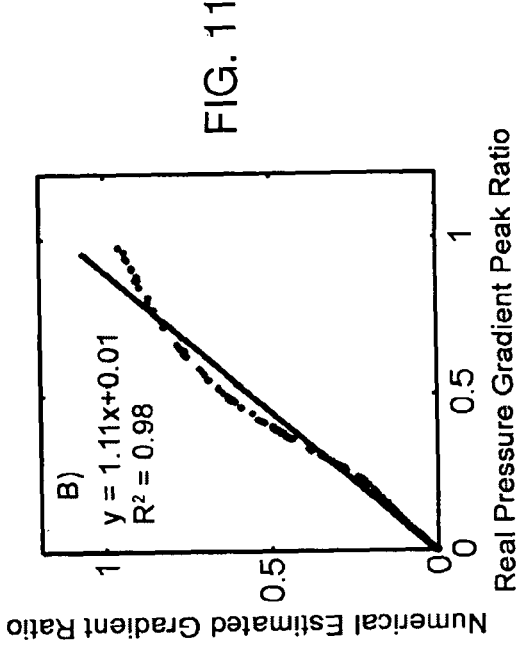
FIG. 10 is a graph showing a numerical example of atrioventricular pressure gradient that generates an E-wave.
Figure 11:
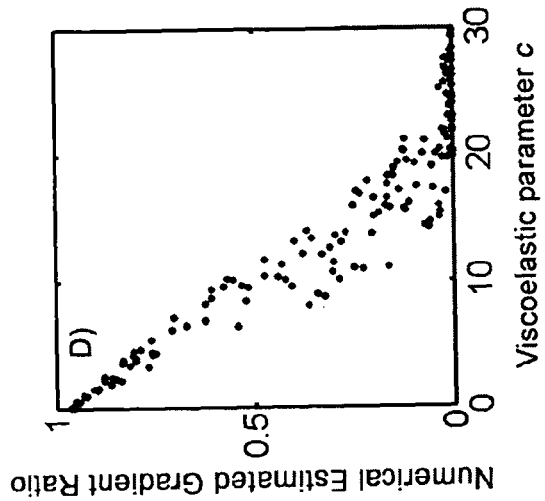
FIG. 11 is a graph showing a correlation between a simulated pressure gradient peak ratio and a numerical estimated pressure gradient peak ratio by evaluating pressure ratio at times DT+AT/2 and DT/2.

Equation (19) may be used in Equation (12) for PPGR. In order to simplify this expression, it may be noticed that the peak positive pressure gradient occurs near a time t=DT+AT/2, and the peak negative pressure gradient occurs near t=DT/2 (where t=0 at MVO), since the pressure gradient is similar to a sinusoidal function with decreasing oscillation peaks, as shown in FIG. 10. Numerical simulation with 180 randomly picked physiologic c and k values was performed to confirm this simplification. The result of these numerical simulations showed that the peak pressure gradient recovery ratio measured at these two estimated time points is a reasonable approximation to the value of the peak pressure gradient recovery ratio at the actual peaks of the gradients, shown in FIG. 11. With this assumption, PPGR becomes:

$$PPGR = \left|\frac{\Delta P_{DT+AT/2}}{\Delta P_{DT/2}}\right| \quad \text{Eq. (20)}$$

$$= \exp\left(-\frac{c(AT+DT)}{2}\right) \frac{\dfrac{1}{1+c/2\sqrt{k}} - \dfrac{\sqrt{2k}}{c} e^{\frac{cAT}{4}} \dfrac{(1+c/\sqrt{k})}{\sqrt{1+c/2\sqrt{k}}}}{\dfrac{1}{1-c/2\sqrt{k}} + \dfrac{\sqrt{2k}}{c} e^{-\frac{cDT}{4}} \dfrac{(1-c/\sqrt{k})}{\sqrt{1-c/2\sqrt{k}}}}$$

This expression can be consolidated by substituting $$y = \frac{c}{2\sqrt{k}} \text{ as:}$$

$$PPGR = \exp\left(-\frac{c(AT+DT)}{2}\right) \frac{\dfrac{1}{1+y} - \dfrac{1}{y\sqrt{2}} e^{\frac{cAT}{4}} \dfrac{(1+2y)}{\sqrt{1+y}}}{\dfrac{1}{1-y} + \dfrac{1}{y\sqrt{2}} e^{-\frac{cDT}{4}} \dfrac{(1-2y)}{\sqrt{1-y}}} \quad \text{Eq. (21)}$$

Figure 12:
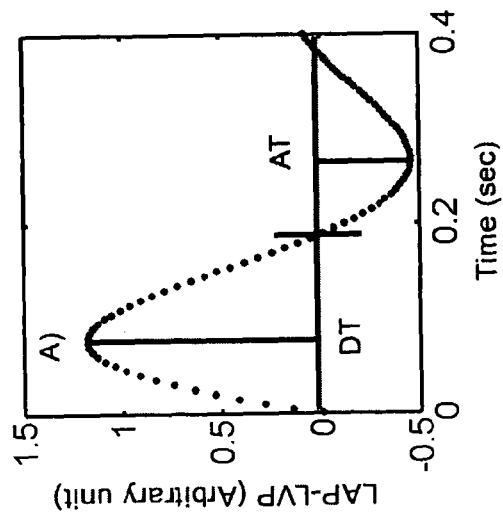
FIG. 12 is a graph showing a relationship between a numerically estimated peak pressure gradient ratio and $$y = \frac{c}{2\sqrt{k}}.$$

For the clinical data analyzed, underdamped (355 out of 363 waves) E-waves had y values between 0.3 and 1.0. Thus PPGR becomes a function of y, and a MATLAB numerical simulation was performed whereby the relationship of PPGR to y was visually assessed. FIG. 12 shows the strong linear relationship between PPGR and y. Thus, the PPGR, which may be used as a numerical surrogate for the PRR, is predicted to be linearly related to $$y = \frac{c}{2\sqrt{k}}.$$

Figure 13:
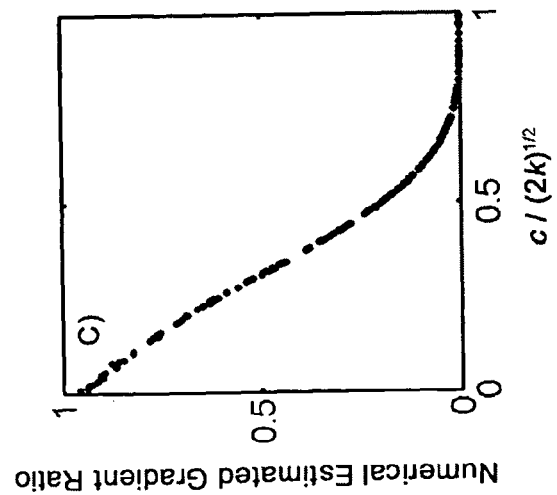
FIG. 13 is a graph showing a relationship between a numerically estimated peak pressure gradient ratio and an E-wave derived relaxation/viscoelastic parameter c.

To assess the relationship between PPGR and c alone, 180 random combinations of c and k were chosen and calculated the expression in Equation (20). FIG. 13 shows the strong linear relationship between PPGR and c for these random (k and c) combinations. Because the range of c values is much wider than the range of k values, and because the PPGR is a reasonable surrogate for the PRR, a strong negative linear relationship exists between PRR and relaxation/viscoelastic parameter c similar to the one derived and observed in FIG. 13.

Figure 14:
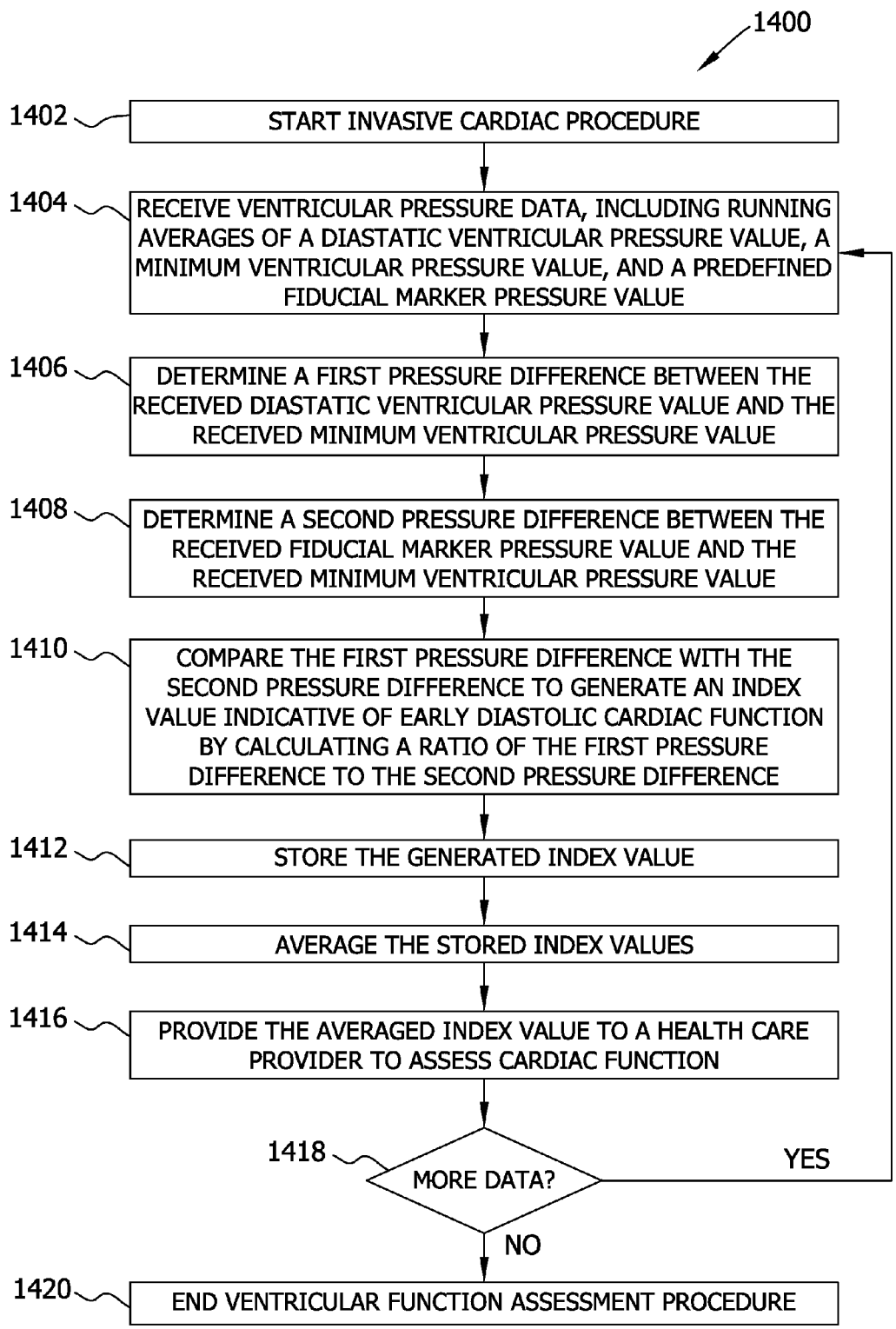
FIG. 14 is a flowchart illustrating an exemplary method of generating an index value that is indicative of ventricular function.

FIG. 14 is a flowchart that illustrates a method 1400 for generating an index value (e.g., PRR) that is indicative of ventricular function, ventricular viscoelasticity, ventricular relaxation, valvular function, ventricular efficiency, and ventricular energetics. Method 1400 includes beginning 1402 an invasive cardiac procedure, such as a cardiac catheterization. Method 1400 also includes receiving 1404 ventricular pressure data during an invasive cardiac procedure, such as a cardiac catheterization. The received pressure data includes a diastatic ventricular pressure value, $P_{Diastasis}$, a minimum ventricular pressure value, $P_{Min}$, and at least one predefined fiducial marker pressure value. The fiducial marker pressure value may correspond to one or more of an end diastolic pressure value, $P_{EDP}$, or a pressure value at the steepest slope of a pressure contour derived from the ventricular pressure data, or both, or any isovolumic pressure value identified by an operator. For example, the operator may select particular values from the obtained pressure contour to correspond to each of the diastatic ventricular pressure value, $P_{Diastasis}$, the minimum ventricular pressure value, $P_{Min}$, and the fiducial marker pressure value. The received ventricular pressure data may include left ventricular pressure data, right ventricular pressure data, or both. The received ventricular data may also include running averages of the diastatic ventricular pressure value, the minimum ventricular pressure value, and/or the predefined fiducial marker pressure value. Further, the PRR may itself correspond to an average of PRR calculations over any quantity of heartbeats, or any quantity of PRR calculations using different pressure values (e.g., different values for the fiducial marker pressure value.

Method 1400 also includes determining a first pressure difference 1406 between the received diastatic ventricular pressure value and the received minimum ventricular pressure value. A second pressure difference is also determined 1408 between the received fiducial marker pressure value and the received minimum ventricular pressure value. The first and second pressure differences are compared 1410 to generate an index value that is indicative of early diastolic cardiac function. The index reflects a ratio of the first pressure difference to the second pressure difference.

The index value is then stored 1412 in a memory. As additional ventricular pressure data is received 1404, and additional index values are generated, the stored index values are averaged 1414.

Each individual index value and/or the averaged index value is then provided 1416 to a health care provider to assess cardiac function. When additional ventricular pressure data is unavailable 1418, the invasive cardiac procedure or, more specifically, the ventricular function assessment procedure, is ended 1420.

A powerful tool readily available to clinical and research cardiologists is noninvasive Doppler echocardiography. Doppler echocardiography allows for the rapid measurement and visualization of the transmitral blood velocity contour. In conjunction with numerous clinical findings, cardiologists use features of a patient's transmitral blood velocity contour to help diagnose and treat numerous cardiovascular disorders. Examples of typical transmitral blood flow velocity contours are presented in FIG. 15.

Figure 15:
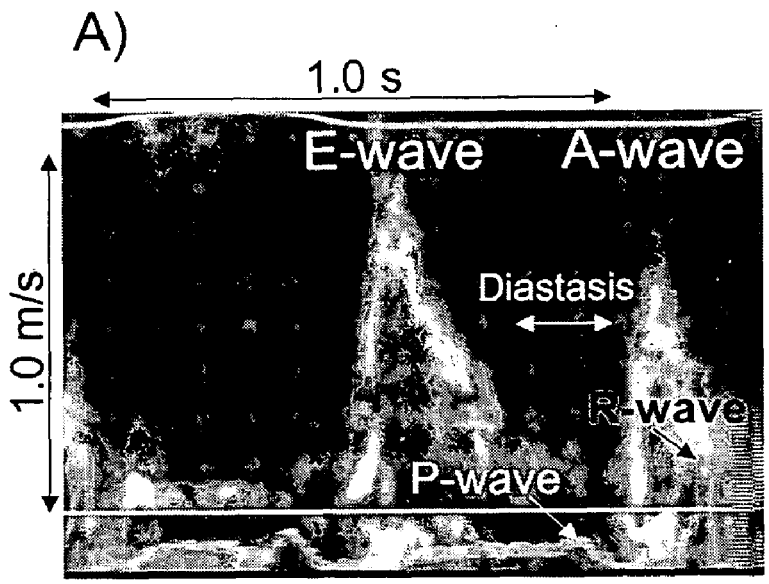
FIG. 15 is a view of an echocardiographically-derived exemplary transmitral velocity contour for a single beat, with a simultaneous 3-lead ECG signal.

FIG. 15 shows that the transmittal blood flow velocity contour includes at least three distinct phases. It is important to note that positive velocities in FIG. 15 represent blood flowing from the atrium and into the ventricle. The first positive wave is called the early filling velocity wave, or simply E-wave. From a physiological perspective, the E-wave represents suction initiated filling, because the blood acceleration during the E-wave is due to an atrioventricular pressure gradient that results from a dropping ventricular pressure relative to a time-delayed and more slowly dropping atrial pressure. In other words, during the E-wave, the ventricle behaves as a suction pump, because the pressure gradient driving flow results from a decreasing sink pressure despite a more slowly declining source pressure.

The second phase of the transmittal velocity profile is defined by the interval between the first and second velocity waves, and is called the diastasis interval. For filling beats occurring at high heart rates (>90 beats per min) the first and second velocity waves may merge together, thereby eliminating the diastasis interval. When present, the diastasis interval represents a no-flow condition. In fact, the ventricle is in mechanical equilibrium during diastole, because atrial and ventricular pressures are equilibrated, and no net blood flow or wall motion occurs during this interval.

The third phase of the transmittal velocity profile includes the second distinct positive velocity wave, and is called the atrial filling, or A-wave. As mentioned above, patients with elevated heart rates often exhibit merged E-wave and A-wave. As heart rate increases, the degree of merging becomes more significant, and at significantly elevated heart rates (on average >120 bpm) the E- and A-waves may merge completely constructively and appear as a single, large wave. From a physiological perspective, the A-wave does not represent suction-mediated filling, because blood accelerates from a pressure gradient that is due to atrial contraction. In other words, during the A-wave the ventricle does not behave as a suction pump because the pressure gradient driving flow results from contraction mediated pressurization of the source (atrium). In other words, the atrium pushes the blood into the ventricle.

Figure 16:
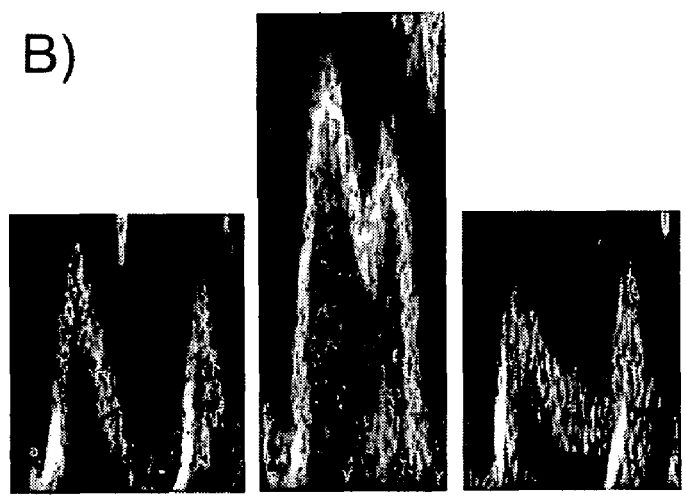
FIG. 16 is a view of an exemplary E-wave and an exemplary A-wave from each of three different patients.
Figure 17:
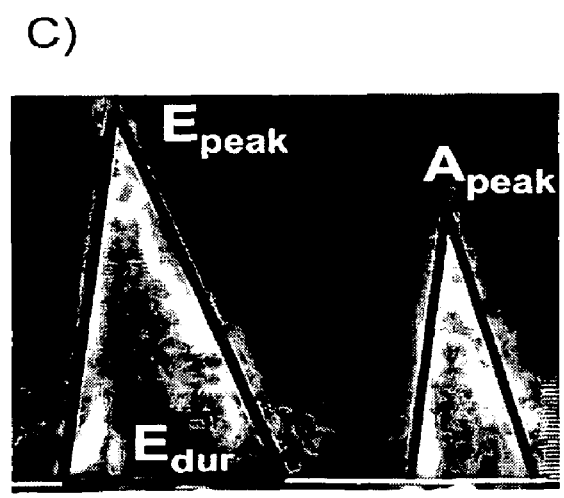
FIG. 17 is a view of an exemplary E-wave and an exemplary A-wave contour fit by basic triangles.

FIG. 16 demonstrates a variety of E-wave and A-wave contour patterns. These patterns are used in practice for phenotypic characterization of cardiovascular physiology, especially diastolic pathophysiology. Current clinical methodology for analysis of E-waves and A-waves however is quite coarse grained; finer details of E-wave and A-wave features such as curvature are discarded and simple triangular geometric approximations to the E-wave and A-wave shapes are instead employed, as shown in FIG. 17.

While echocardiography is widely employed in the evaluation of cardiac patients, invasive catheterization represents another widely employed tool available to cardiologists. In fact, the gold standard for determining the filling ability of the heart (diastolic function) is the determination of the left ventricular end diastolic pressure (LVEDP) by means of left ventricular catheterization. Ventricular catheterization involves the introduction of a pressure recording catheter into a patient's left ventricle. A typical real-time catheterization determined left ventricular pressure (LVP) profile is presented in FIG. 18. Just as with the E-waves and A-waves, specific measures derived from the left ventricular pressure profile are used by cardiologists for diagnosis and treatment of cardiac disease including diastolic dysfunction.

Figure 18:
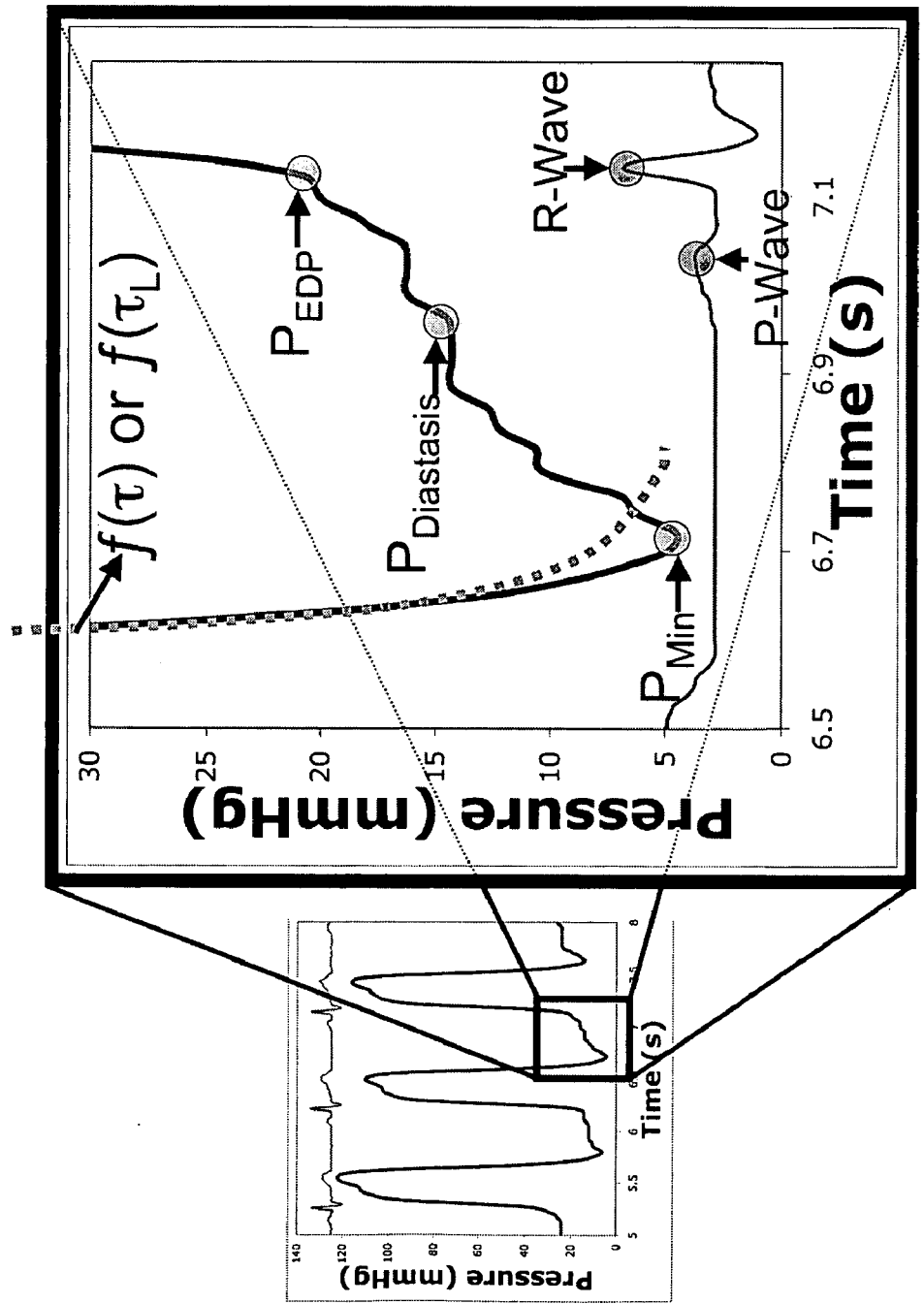
FIG. 18 is a view of an exemplary real-time LVP and simultaneous ECG signal as seen in a catheterization lab during a procedure.

FIG. 18 indicates several of the clinically relevant measures derived from the LVP profile. As discussed above, these measures include the LVEDP and the time constants of isovolumic relaxation, $\tau$ or $\tau_L$. Taken together, Doppler echocardiography and left ventricular catheterization can provide a more complete assessment of a particular patient's cardiac function and, in particular, the patient's diastolic function.

Though simultaneous Doppler-echocardiography and left-ventricular catheterization is possible, it is rarely performed in clinical practice because of the desire to reduce catheterization (arterial access) time. However, the E-wave may provide additional information about diastolic function that is not available from just catheterization. Thus, a method by which an E-wave could be estimated from an LVP profile alone in real time would be of great benefit. Using the PRR index described above, it is possible to generate and display, in real-time, the E-waves corresponding to specific LVP profiles from individual beats. Thus, an automated algorithm may be devised and operated using only the data acquired during catheterization to derive what the E-wave velocity contour would have been had a simultaneous Doppler echocardiogram been performed. Such a method may be referred to as "PRR-based In-Silico Echocardiography".

The E-wave and A-wave velocity contours may be modeled and accurately predicted by the physics of damped simple harmonic motion. The physical underpinnings (parameterized diastolic filling, or PDF model) and numerical methods (model based image processing or MBIP) needed to extract damped harmonic motion parameters from E-wave and A-wave are described above. Many patients have E-wave velocities that exhibit the underdamped regime of damped simple harmonic motion Equation (22):

$$v(t) = \frac{kx_o}{\omega} e^{-\frac{c}{2}t} \sin(\omega t) \qquad \text{Eq. (22)}$$

where k is a spring constant, c is a damping constant, $x_o$ is a multiplicative initial spring displacement, and $$\omega = \sqrt{k - \frac{c^2}{4}}\,.$$

Figure 19:
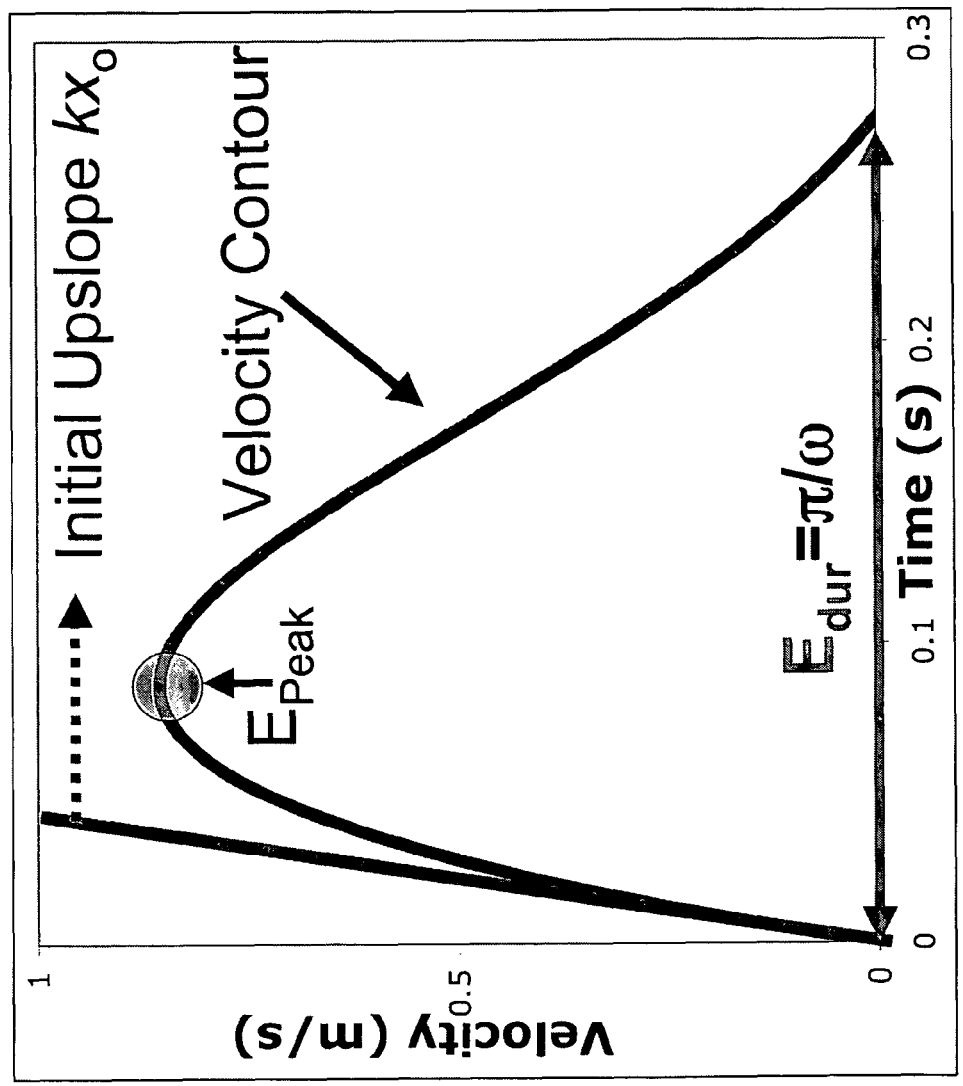
FIG. 19 is a graph plotting Equation (23) versus time for exemplary and arbitrarily chosen k, c, and $x_o$ values in the underdamped region.

FIG. 19 provides a plot of Equation (22). The initial upslope, or mass normalized initial driving force, is numerically given by the product $kx_o$. Furthermore, the width of the wave ($E_{dur}$) is related to the frequency $\omega$ simply by:

$$E_{dur} = \frac{\pi}{\omega} \qquad \text{Eq. (23)}$$

It should be noted that Equation (22) is fully determined if one can determine the quantities $\omega$, $kx_o$, and c. Thus, to estimate the E-wave from the LVP contour, methods are necessary by which $kx_o$, $\omega$, and c may be easily determined. Previous and current work suggests that the E-wave parameters of interest ($kx_o$, $\omega$, c) may be determined if the following hemodynamic parameters from the LVP contour and ECG are found: the LV end-diastolic time and pressure ($t_{EDP}$, $P_{EDP}$), the diastasis pressure ($P_{Diastasis}$), the mitral valve opening time and pressure ($t_{MVO}$, $P_{MVO}$), the LV minimum pressure and time ($t_{Min}$, $P_{Min}$), and the E-wave end time or time at which diastasis begins ($t_{DiastasisStart}$). It should be noted that this analysis requires that subjects do not have significantly elevated heart rates, and that subjects posses P-waves in their ECG signal. Thus, subjects in atrial fibrillation can not currently be analyzed using these methods.

To estimate the E-wave from the LVP contour, the PRR is used to determine the damping constant c of the E-wave. As described above, a strong linear relationship is presented between the PRR and the damping constant, c. This regression enables a calculation of c given the PRR:

$$c = -19.2(PRR) + 26.6 \qquad \text{Eq. (24)}$$

The PRR may be easily calculated in a real-time fashion from the LVP profile, and therefore the damping constant c may be simply calculated from Equation (24). It is important to note that the linear correlation presented in Equation (24) ($R^2 = 0.79$) may be adjusted so that the x-intercept of the c vs. PRR plot crosses (1,0). Such an adjustment leaves results in a linear regression between c and PRR with $R^2 = 0.75$.

The next step in estimation of the E-wave involves the estimation of the initial E-wave upslope, $kx_o$. Previous published work has demonstrated a strong linear relationship between the echocardiographically determined $kx_o$ value and the (simultaneously) catheterization determined pressure difference between LVEDP and minimum LVP. This regression provides an equation for determining $kx_o$ (in units of m/s²) from LVP profile measures alone:

$$kx_o = 0.407(P_{EDP} - P_{min}) + 15.40 \qquad \text{Eq. (25)}$$

Figure 20:
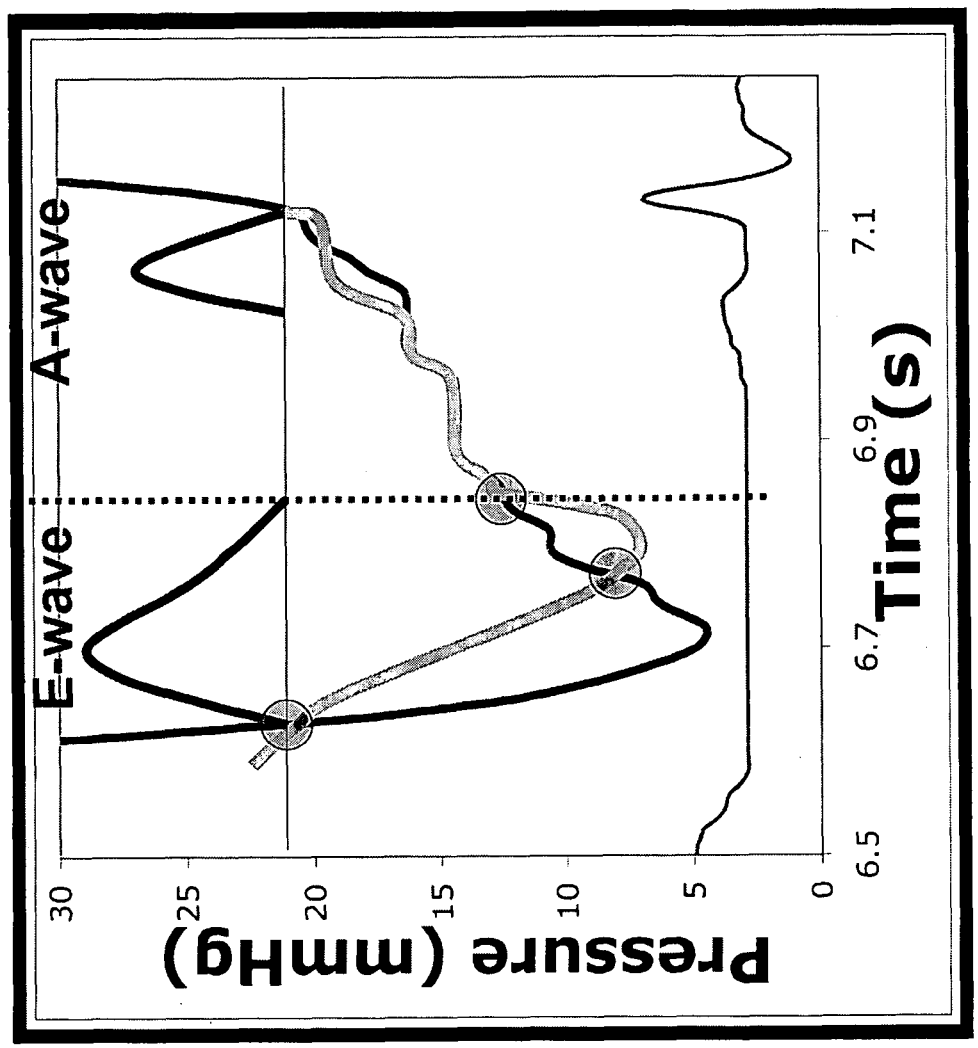
FIG. 20 is a graph showing simultaneous exemplary left ventricular pressure, left atrial pressure, a Doppler E-wave, a Doppler A-wave, and ECG data for one particular beat.

The next step involves the calculation of the frequency, $\omega$. Using Equation (23), the frequency may be calculated if the E-wave duration, $E_{dur}$, is estimated. There are several methods by which the duration of the E-wave may be approximated. One method for $E_{dur}$ determination includes placing a pressure catheter in the atrium and ventricle. FIG. 20 shows a representative hemodynamic pressure and flow data from such a procedure. As is evident from FIG. 20, the E-wave start corresponds to the first atrioventricular pressure crossover, and the end of E-wave flow is causally coupled with the third equalization of atrial and ventricular pressures after mitral valve opening. However, because obtaining atrial pressures in the catheterization lab is impractical, a different methodology is necessary.

To aid in analysis, previous results regarding the mechanical duration of diastole as a function of heart rate may be applied. Grounded in the physics of simple harmonic oscillation, previous work predicted and demonstrated a robust correlation ($R^2 = 0.98$) between the mechanical duration of diastole (MDD) in milliseconds and heart rate (HR), where MDD is defined as the interval between E-wave start and A-wave end ($t_{EDP} - t_{MVO}$). This relationship is given in Equation (26):

$$MDD = -549 + 2.13\, HR + \frac{61500}{HR} \qquad \text{Eq. (26)}$$

The HR, in beats per minute may be determined by dividing 60 by the particular beat's R-peak to R-peak time interval (in seconds), and this value can be plugged into Equation (26) to determine the MDD. Finally, by taking the time of the R-wave peak to be the particular beat's end diastolic time, the start of the E-wave and the mitral valve opening time ($t_{MVO}$) may be determined by subtracting the MDD from the R-wave peak time.

An effective strategy for determination of $E_{dur}$ involves determining the E-wave start-time and end-time, and simply taking the difference of these two time points. Two simple methods, among others, may be employed to determine the E-wave start-time. First, the simplifying assumption may be made that the pressure at mitral valve opening and E-wave start is nearly equivalent to the end-diastolic pressure. Thus, the time of mitral valve opening and therefore start of the E-wave can be taken to be the time at which the decreasing LVP profile is equal to the ensuing LVEDP. A second possible method for determining the E-wave start time takes advantage of the strong correlation between MDD and HR presented in Equation (26). As discussed above, the E-wave start time is then given by the MDD subtracted from the R-wave peak-determined or otherwise-determined LVEDP time. Once the start of the E-wave is determined, the only task remaining is the determination of the E-wave end-time.

Cardiac cycles with RR intervals above 800 ms (<90 beats per minute) typically have a clear diastasis interval separating E-waves and A-waves. Previous published work has demonstrated a strong correlation between HR and time duration of the diastasis interval. This relationship holds even for slightly merged E-waves and A-waves (heart rates between 100-120), where the diastasis time interval is negative. Thus, one can easily estimate the interval (in milliseconds) between an E-wave and an A-wave:

$$\Delta t_{Diastasis} = 4.40(HR) + 65500\left(\frac{1}{HR}\right) - 1150 \qquad \text{Eq. (27)}$$

Furthermore, the start of the A-wave occurs simultaneously with the ECG P-wave. Current catheterization labs routinely employ automated ECG pattern detection algorithms to detect, among other things, P-waves and R-waves. Because the ECG signal and the LVP profile are synchronized in the catheterization lab, automated detection of and P-waves and R-waves allows for automated determination of A-wave start times, as well as diastasis pressures and LVEDP.

Thus, the E-wave end-time is calculated by traveling backwards in time on the pressure contour, that is, by determining the time of the P-wave peak, which corresponds to the onset of the A-wave, and subtracting the diastasis interval time determined from Equation (27). Once we have the E-wave end-time, the E-wave duration is calculated as the difference between E-wave end-time and E-wave start time. Finally, with the $E_{dur}$ calculated, Equation (23) is utilized to determine the frequency, $\omega$.

$$\omega = \frac{\pi}{(t_{ECG\,P-wave} - \Delta t_{Diastasis}) - t_{E-wave\,start}} \qquad \text{Eq. (28)}$$

Figure 21:
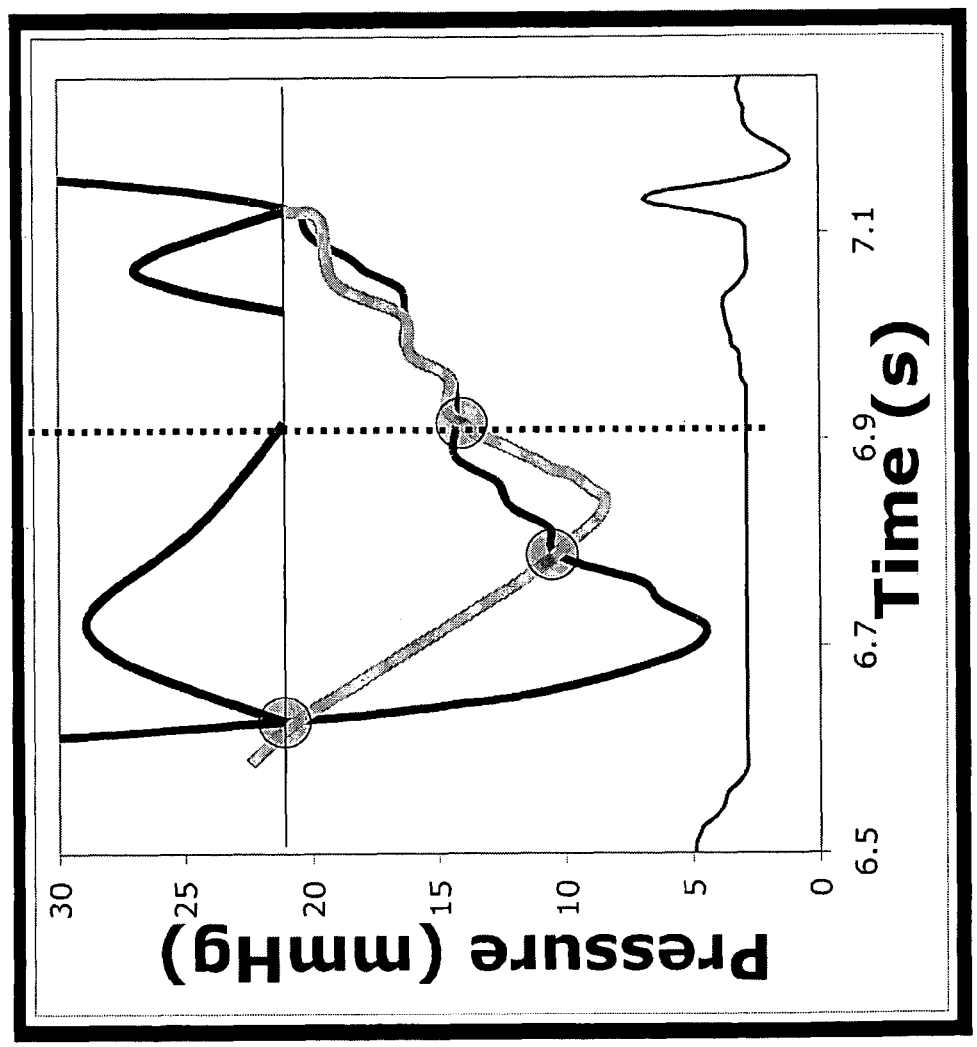
FIG. 21 is a graph showing simultaneous exemplary left ventricular pressure, left atrial pressure, a Doppler E-wave, a Doppler A-wave, and ECG data for one particular beat, wherein diastasis begins after a flat portion of the LVP contour commences.

Another possible estimate of the E-wave-end time may be made by considering the flat (i.e. diastatic) portion of the LVP profile. To be sure, the flat portion of the LVP profile does not necessarily represent the full diastatic interval, because diastasis requires the absence of a pressure gradient, and the atrioventricular pressure gradient crossover may not occur until after the LVP profile flattens out, as shown in FIG. 21, or may occur before some major flat regime begins, as shown in FIG. 21. However, the use of multiple methods to estimate the E-wave end time is advantageous because it provides upper and lower limits to the resulting E-waves, and thereby enables overdetermination. The simplest method for determining the start of the LVP flat interval is a basic thresholding procedure. With this method, the start of the LVP flat interval is the time at which the LVP recoils to a pressure within a 1-2 mmHg, or some suitable threshold, of the previously determined diastasis pressure ($P_{Diastasis}$).

Figure 22:
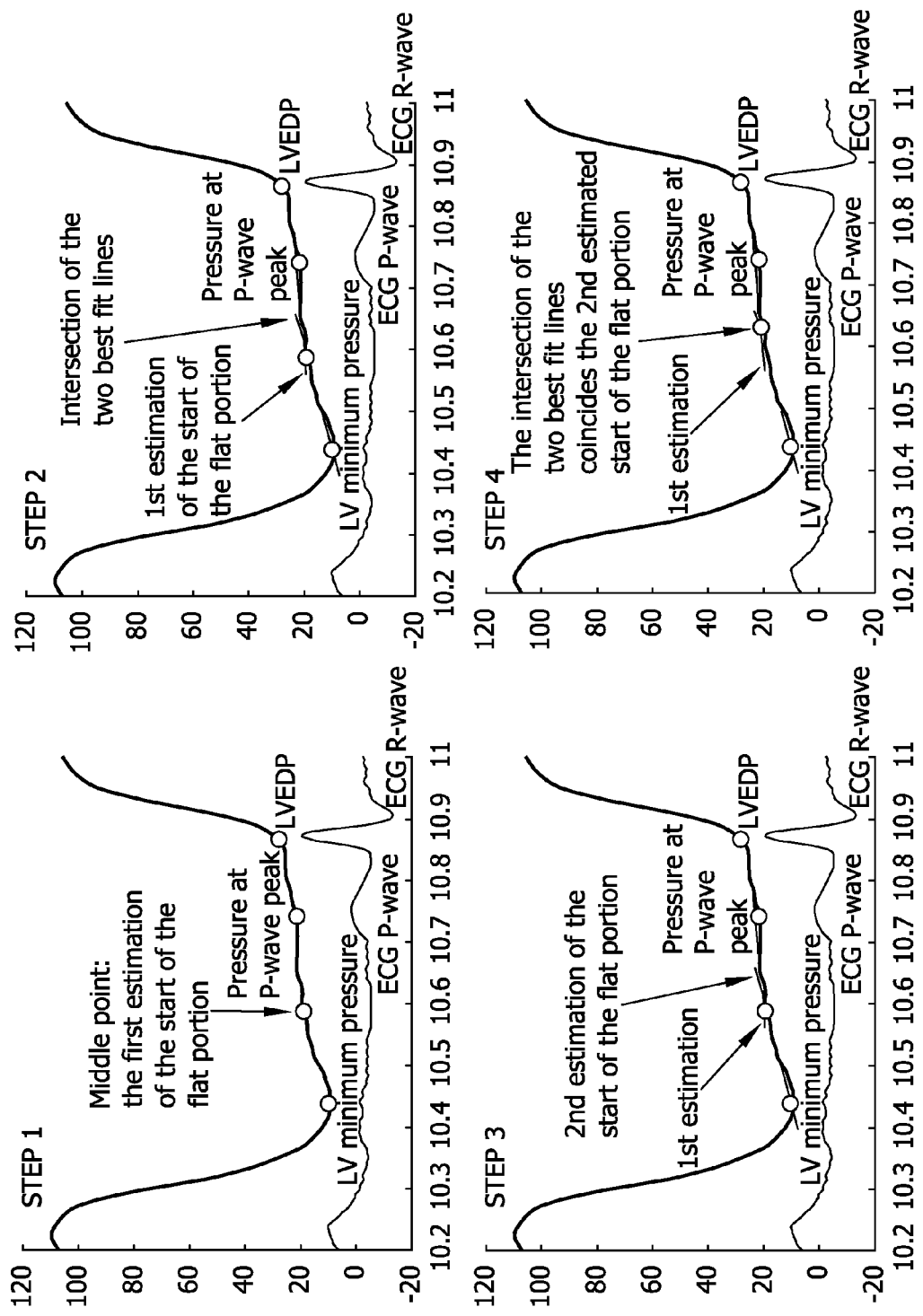
FIG. 22 shows an exemplary iterative approach for determining the start of an LVP contour.

Alternatively, one can determine the LVP flat interval start through an iterative approach. A first guess of the LVP flat interval start is estimated as the midpoint time between LV minimum pressure and P-wave peak. The iterative approach creates a least squares best fit line to the pressure contour between the minimum pressure and previous guess point, and a second least squares best fit line to the pressure contour between the previous guess point and the P-wave peak. The next estimate for the time of the start of the LVP flat interval is then taken to be the intersection of the two best fit lines created in the previous step. This process is iterated until one converges on one point, or on a stable cycle of a set of points. If the convergence is toward a set of points, then the start of the LVP flat interval is taken to be the average of these points. This process is visually detailed in FIG. 22.

The iterative approach is a more robust method than simply applying a threshold of 1-2 mmHg relative to a determined diastasis pressure, because in certain cases the so called "flat LVP portion" may not be completely flat, and instead may show a gradual change of 1-5 mmHg with respiration. For example, a large inspiration during a diastasis interval will tend to slightly decrease the LV pressures, thereby making the thresholding procedure less reliable, and the iterative approach more favorable. In addition, often clinical data may possess several small regions that appear to be flat, and therefore it is not obvious as to which flat region to pick. This is seen somewhat in the data presented in FIG. 18, and in such cases the iterative approach to determining the end of the E-wave is preferred.

Instead of using $E_{dur}$ in order to determine the frequency, $\omega$, we can instead use previously published relationships between frequency $\omega$ and E-wave deceleration time (DT) to determine $\omega$, as shown:

$$DT = \frac{\pi}{\omega} - \frac{1}{\omega} a\tan\left(\frac{2\omega}{c}\right) \qquad \text{Eq. (29)}$$

where c has already been determined above from the hemodynamic data alone.

Using Equation (29) enables a solution for $\omega$ based on a known DT. Thus, DT must be estimated from the LVP contour and ECG data alone. This can be achieved by taking the difference between the catheterization estimated E-wave end time and E-wave peak time.

One approximation is that the peak of the E-wave occurs at the minimum of the LVP contour. This is justified by the fact that the first atrioventricular crossover in pressure occurs at a time DT after mitral valve opening, and is often beyond the minimum pressure. Thus the time interval between minimum pressure and the catheterization estimated E-wave end time is a reasonable estimate to the E-wave DT. Furthermore, it is a trivial computational task to determine the time at which the LVP contour is minimized for a particular beat.

DT is calculated based on the difference between the two times found as discussed. Then, using the previously determined c from Equation (24) and Equation (29), enables a solution for $\omega$.

Alternatively, one may solve for the spring constant, k, directly, using the approximate expansion of Equation (29) in the low c/(2k) limit:

$$DT = \frac{\pi}{2\sqrt{k}} - \frac{c}{2k} \qquad \text{Eq. (30)}$$

$$\Rightarrow 2DTk - \pi\sqrt{k} + c = 0$$

$$\therefore k = \sqrt{\frac{\pi \pm \sqrt{\pi^2 - 8cDT}}{4DT}}$$

With k calculated, frequency, $\omega$, may be calculated by $$\omega = \sqrt{k - \frac{c^2}{4}},$$

where c is already determined from the PRR as in Equation (24), and DT is determined as above.

Figure 23:
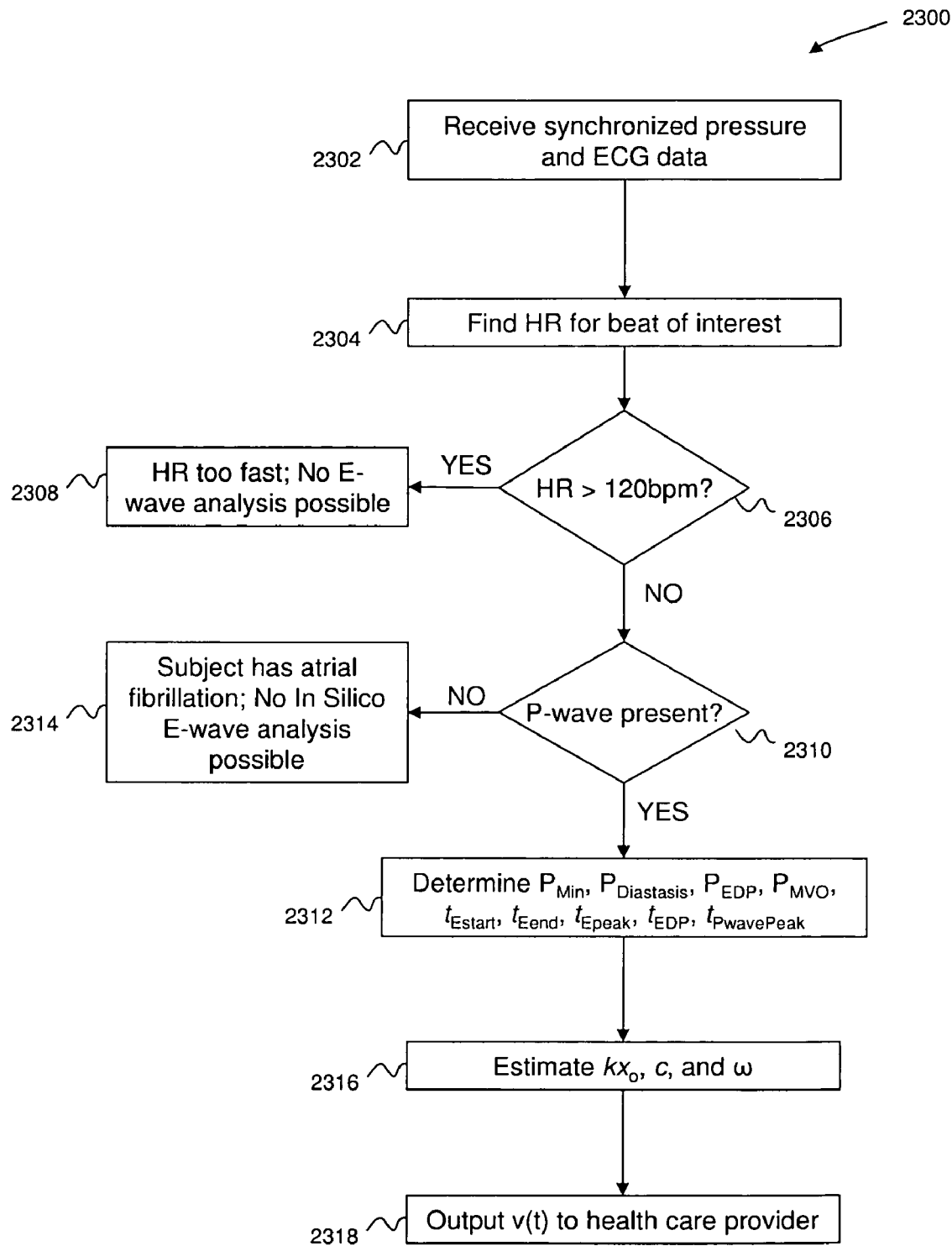
FIG. 23 is a flowchart illustrating an exemplary method for generating a simultaneous E-wave velocity contour given synchronized LVP and ECG data.

FIG. 23 shows a flowchart illustrating a method for the determination of E-wave contours from LVP contours. The following is an example of the method shown in FIG. 23 using the data presented in FIG. 18. Synchronized pressure and ECG data are received 2302. A heart rate for a beat of interest is found 2304 using automated ECG pattern detection techniques which are widely available in the clinical setting, and the R-waves that flank the filling interval are determined. If the heart rate is found 2306 to be greater than approximately 120 beats per minute, the resulting RR interval is too small for measuring an E-wave and the method ends 2308 until the heart rate slows. For the data in FIG. 18, the resulting RR interval is 930 ms, which gives a HR of 64.52 beats per minute. This is well within the regime of unmerged waves. If the hear rate is found 2306 to be less than approximately 120 beats per minute, and if a P-wave is present 2310 various hemodynamic parameters are determined 2312. If no P-wave is present 2310, meaning that the subject has atrial fibrillation, then PRR-based In Silico E-wave analysis is not possible and the method ends 2314.

The end-diastolic pressure, $P_{EDP}$, is determined. Because there is no evidence of AV block, the $P_{EDP}$ is the pressure at the peak of the R-wave, which is 23.72 mmHg, or the pressure at the start of the R-wave, which is 20.28 mmHg. In the presence of AV block one would have to calculate the maximum pressure between the R-wave peak and the minimum pressure point to determine $P_{EDP}$. By maintaining two estimates for $P_{EDP}$ the determination of lower and upper bounds for the resulting E-wave is allowed for. The assumption is made that mitral valve opening pressure equals end-diastolic pressure and, therefore, it is determined that the E-wave start time in FIG. 18 must be either at $t_{Estart}$=6.624 s, or $t_{Estart}$=6.622 s, depending on if the peak R-wave or start of R-wave determined PEDP pressure is used as a reference. Furthermore, the determined HR may be used in Equation (25) to determine the MDD. The MDD is thus determined to be 541.7 ms. Again, it is known that diastole ends at either the peak of the R-wave or the start of the R-wave, then subtracting MDD shows that the E-wave start and mitral valve opening occurs at $t_{Estart}$=6.564 or $t_{Estart}$=6.594, respectively. Thus multiple estimates for the E-wave start time are obtained.

Next the minimum pressure is determined, by searching for the minimum pressure found in the chosen R-R interval. The minimum pressure shown in FIG. 18 occurs at a time $t_{Min}$=6.716 s and is $P_{Min}$=4.47 mmHg.

Next the diastasis pressure, $P_{Diastasis}$, is determined. Taking into consideration the presence of a P-wave, and through ECG detection algorithms, the peak of the P-wave is determined to be at $t_{Pwavepeak}$=7.031 s, with a simultaneous LV pressure of $P_{PwavePeak}$=16.3 mmHg. Because the P-wave peak marks the beginning of A-wave flow, the diastasis pressure may be estimated as simply being the pressure at the P-wave peak, and thus a first estimate of $P_{Diastasis}$ is $P_{Diastasis}$=16.30 mmHg. Also the pressure at the start of the P-wave rather than the P-wave peak is considered, which is $P_{Diastasis}$=14.37 mmHg. Next the iterative approach detailed above is applied for determination of E-wave end time. This method converges on $t_{Eend}$=6.851, and a concurrent diastasis pressure of $P_{Diastasis}$=12.5 mmHg. If the iterative method is applied with the P-wave start as a reference point instead of the P-wave peak, then $t_{Eend}$=6.856, and a $P_{Diastasis}$=12.6 mmHg. The refined diastasis pressure is then the average of these values, and is therefore $P_{Diastasis}$=14.0 mmHg. Averaging over multiple values only serves to overdetermine and average out any systematic errors or biases associated with one particular method. It is not generally necessary to calculate so many approximations to the diastasis pressure, and in practice only one or two estimations may be necessary. Alternatively, one may simply calculate the duration of diastole (DD) as defined in Equation (28), and determine the start of diastasis by simply subtracting DD from the P-wave peak time. Plugging in for HR it may be determined that DD=149.1 ms, and this yields $t_{Eend}$=6.882 s. Then the diastasis pressure may be estimated as the average pressure between $t_{Eend}$ and $t_{PwavePeak}$. The average pressure between t=6.882 s and t=7.031 s is 15.03 mmHg, and thus another estimate is $P_{Diastasis}$=15.03 mmHg.

With these calculations c, $kx_o$, and ω may be determined 2316. First, c is determined by calculating the PRR, which is described in more detail above. Using the value for $P_{Min}$ and the various estimates for $P_{EDP}$ and $P_{Diastasis}$, PRR may be 0.49, 0.60, 0.55, or 0.67. Using Equation (22), c is either 17.11 1/s, 15.05 1/s, 16.07 1/s, or 13.78 1/s respectively. The average PRR is 0.58 and the average c is 15.50 1/s.

Next the $kx_o$ value is determined. Using the value for $P_{Min}$ and the possible values for $P_{EDP}$, ΔP is calculated to be 19.25 mmHg or 15.81 mmHg. These pressure differences correspond, using Equation (23), to $kx_o$ values of 23.23 mN or 21.83 mN, with an average value of 22.53 mN.

The frequency, ω, is determined. In determining the diastasis pressure estimates of $t_{Eend}$ have been found, and in the first few calculations several estimates for $t_{Estart}$ have been determined. Taking the difference between the estimated E-wave end and start times results in possible values for $E_{dur}$, and, by Equation (23), possible values for ω. Using only estimates for $t_{Eend}$ that employ the P-wave peak, $E_{dur}$ may be 0.258 s, 0.26, 0.288 s, or 0.318 s. The corresponding ω values are 12.18 1/s, 12.08 1/s, 10.91 1/s or 9.88 1/s.

Upper bounds, lower bounds, and average values for all the E-wave parameters of interest may be created by considering maxima and minima of the collection of calculated PDF parameters. The lower bound E-wave has ω=9.88 1/s, $kx_o$=21.80, and c=14.25 1/s. The upper bound E-wave has ω=12.18 1/s, $kx_o$=23.20 and c=16.70 1/s. Finally, the average E-wave has ω=11.18 1/s, $kx_o$=22.53, and c=15.25 1/s.

To display any of these E-waves the estimated ω, $kx_o$, and c values are plugged into Equation (22). This leaves still the variable t in Equation (22). The t is determined by generating numerous values between 0 and $E_{dur}$, where $E_{dur}$ is given by the estimated ω value and Equation (23). The t values may be evenly spaced at the sampling period of the raw input LVP data. Finally, t is used to output 2318 the resulting function with appropriate scale on the LVP contour or in a separate display.

Figure 24:
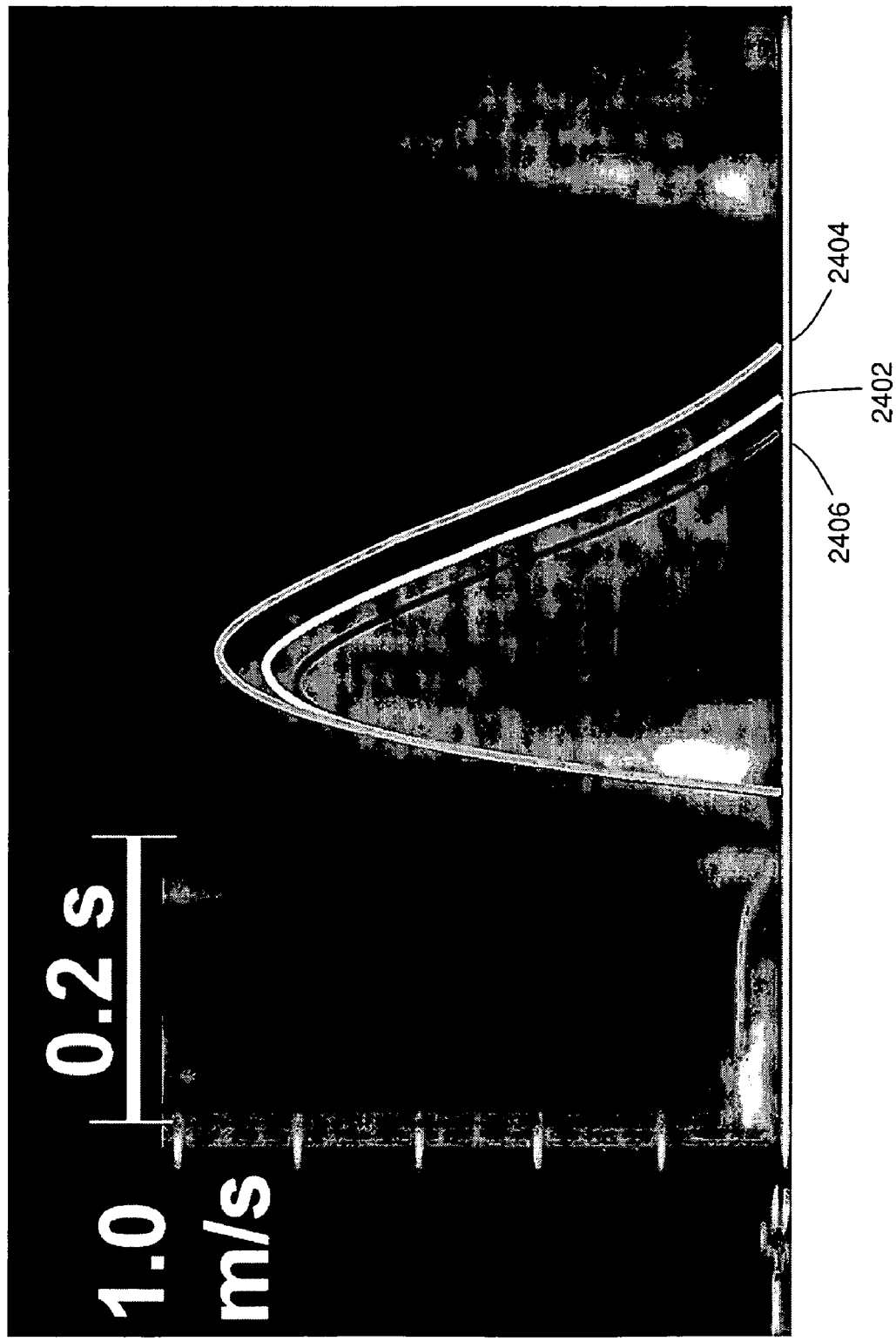
FIG. 24 is a view of an exemplary transmittal Doppler velocity contour measured simultaneously during catheterization for the beat shown in FIG. 18, with superimposed estimated In Silico Echocardiography waves.

For comparison, the resulting upper bound, lower bound, and average E-wave estimated from the LVP contour alone is superimposed on the actual measured Doppler E-wave in FIG. 24. It should be noted that the average E-wave 2402 predicts the true E-wave contour extremely well. Furthermore the upper 2404 and lower bound 2406 E-wave effectively demarcate the location of the true E-wave, and track the deceleration portion curvature fairly well. Thus, FIG. 24 demonstrates how closely an invasively derived E-wave analogue can predict the actual noninvasive Doppler E-wave.

Figure 25:
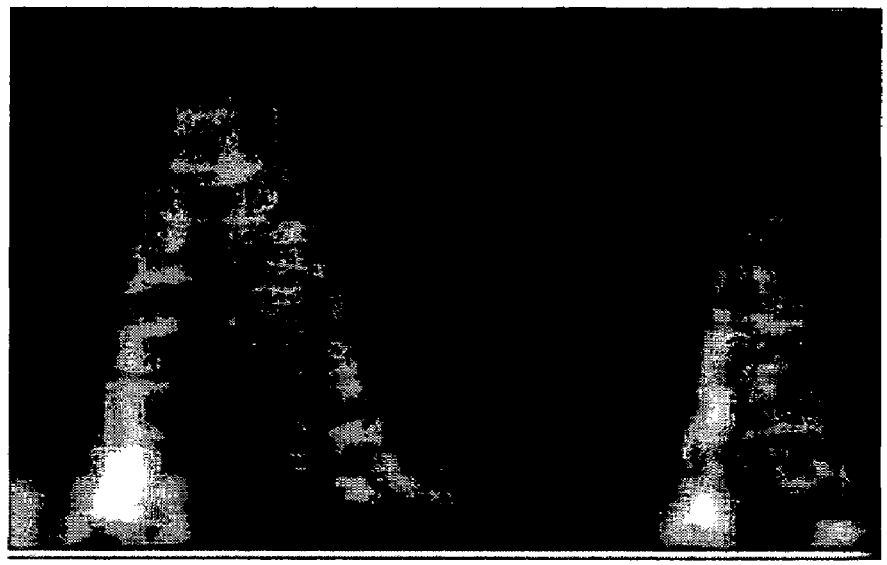
FIG. 25 is a view of an exemplary raw Doppler E-wave obtained during catheterization for the beat shown in FIG. 18.
Figure 26:
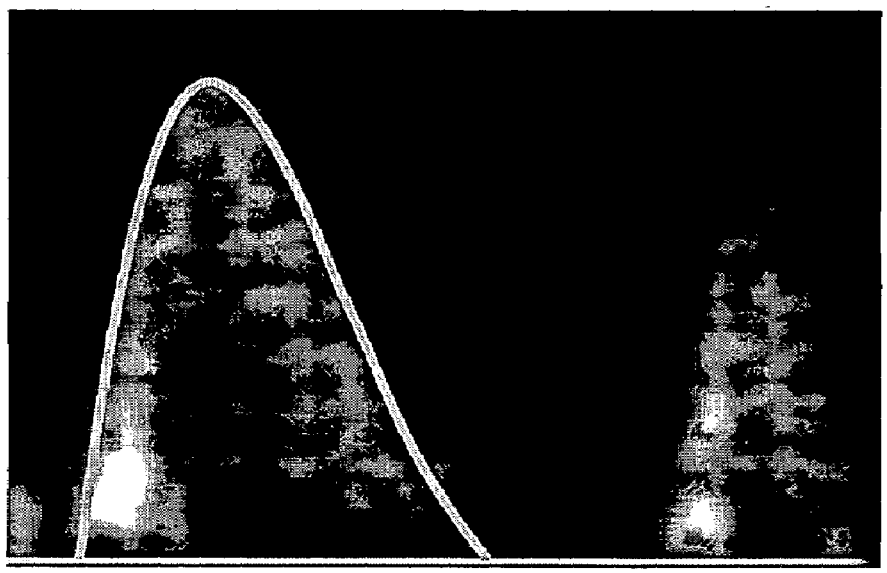
FIG. 26 is a view of the exemplary raw Doppler E-wave shown in FIG. 25 with an exemplary parametrized diastolic filling (PDF) model fit superimposed, as calculated by an independent observer.
Figure 27:
FIG. 27 is a view of the exemplary raw Doppler E-wave and superimposed PDF model fit shown in FIG. 26, including an exemplary superimposed In Silico Echocardiography E-wave derived from an LVP contour.

To independently assess the closeness of fit, a blinded observer applied the PDF formalism to the raw E-wave image from FIG. 24, in order to derive a best-fit velocity contour. FIG. 25 shows the raw E-wave image, and FIG. 26 shows the raw E-wave image superimposed with the model-based best-fit velocity contour. Finally, FIG. 27 shows the best-fit velocity contour superimposed, derived by a blinded investigator, as well as the LVP-contour derived average E-wave 2402 (shown in FIG. 24). The two waves are virtually indistinguishable.

Figure 28:
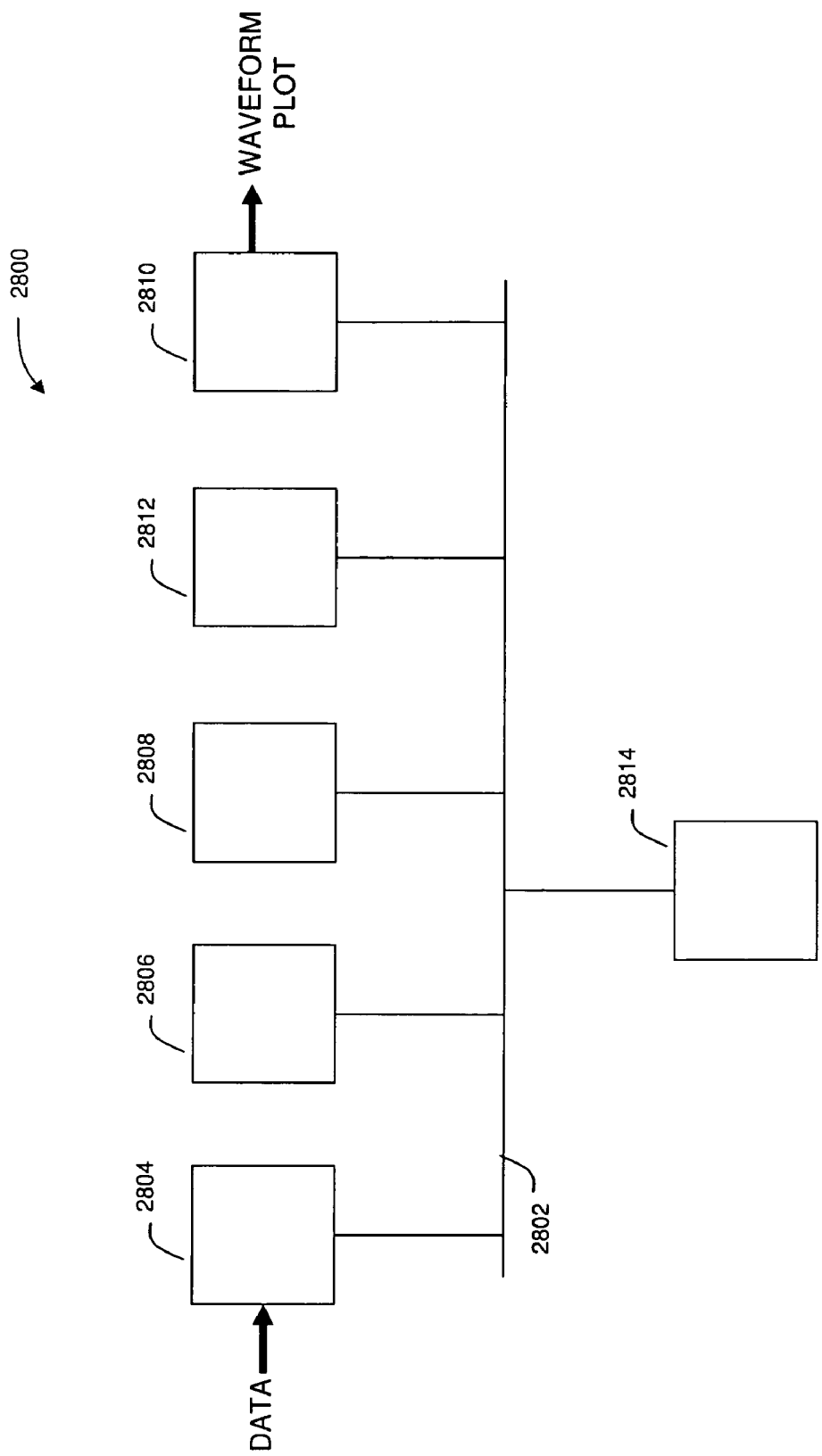
FIG. 28 is a block diagram of an exemplary system for calculating PRR and/or $PRR^{(AFib)}$.

FIG. 28 shows an exemplary system 2800 for calculating the PRR, $PRR^{(AFib)}$, and/or the LVP-contour derived average E-wave. As described above, the PRR is indicative of one or more of the following: ventricular diastolic function, ventricular viscoelasticity, ventricular relaxation, and valvular function. Alternatively, the PRR corresponds to a pressure recovery ratio related to the properties previously mentioned. The elements of system 2800 are each communicatively coupled by, for example, a communications bus or network 2802.

System 2800 constitutes exemplary means for obtaining 2804 the ventricular pressure data for storage in a memory area 2806. Memory area 2806 stores ventricular pressure data that is obtained during an invasive cardiac procedure, such as a cardiac catheterization. The ventricular pressure data includes a diastatic ventricular pressure value, $P_{Diastasis}$, a minimum ventricular pressure value, $P_{Min}$, and a predefined fiducial marker pressure value. System 2800 also includes an exemplary means for defining 2808 the fiducial marker pressure value. The predefined fiducial marker pressure value may be an end diastolic pressure value, $P_{EDP}$, or a pressure value at the steepest slope of a pressure contour derived from the ventricular pressure data.

System 2800 also includes a processor 2810 that is configured to execute computer-executable instructions. Processor 2810 determines a first pressure difference between the diastatic ventricular pressure value and the minimum ventricular pressure value, and also determines a second pressure difference between the fiducial marker pressure value and the minimum ventricular pressure value. In addition, processor 2810 compares the first pressure difference to the second pressure difference to generate an index value indicative of early diastolic cardiac function. The calculation of first pressure difference and the second pressure difference, and the comparison of the first pressure difference to the second pressure difference all occur during the invasive cardiac procedure. Processor 2810 also calculates parameters of an echocardiogram waveform corresponding to the ventricular pressure data stored in memory area 2806 as a function of the generated index value, a spring constant, a damping constant, a multiplicative initial spring displacement, and a frequency. Alternatively, system 2800 constitutes exemplary means for generating 2812 the index value as a function of the first and second pressure differences. The first pressure difference represents recovered pressure during early filling of the ventricle, and the second pressure difference represents lost pressure during early filling of the ventricle. In addition, system 2800 constitutes exemplary means for calculating 2814 the parameters of the echocardiogram waveform.

Processor 2810 also executes computer readable instructions for plotting the resulting echocardiogram waveform based on the calculated parameters. In addition, processor 2810 is configured to calculate a damping constant for the echocardiogram waveform as a function of the generated index value, and to calculate an initial upslope for the echocardiogram waveform as a function of the determined second pressure difference. Further, processor 2810 is configured to calculate a frequency of the echocardiogram waveform as a function of an estimated echocardiogram waveform start time, an estimated echocardiogram waveform end time, and/or an estimated echocardiogram waveform peak time.

The methods described above and shown in FIGS. 14 and 23 may be used with the system described above and shown in FIG. 28. Alternatively, each of the above-described methods may be used with any suitable system and/or one or more computer-readable media having computer-executable components. One such component is an exemplary memory component, such as memory area 2806. The memory component accesses ventricular pressure data stored during an invasive cardiac procedure. The ventricular pressure data may include a diastatic ventricular pressure value, a minimum ventricular pressure value, and/or a predefined fiducial marker pressure value, such as an end diastolic pressure value.

Another such component is an exemplary processor component, such as processor 2810. As described above, the processor component determines a first pressure difference between the diastatic ventricular pressure value and the minimum ventricular pressure value accessed by the memory component, and also determines a second pressure difference between the fiducial marker pressure value and the minimum ventricular pressure value. A ratio of the first pressure difference to the second difference is calculated by an exemplary index component, such as the means for generating an index 2808. The index component uses the calculated ratio to generate an index value indicative of early diastolic cardiac function. Further, an exemplary interface component provides the index value calculated by the index component to a health care provider to assess cardiac function. Each of the processor component, index component, and interface component are executed during an invasive cardiac procedure.

As described herein, a pressure recovery ratio (PRR) enables clinicians to determine ventricular relaxation/viscoelasticity, which is a property of the ventricle that, when abnormal, may be a sign of disease. The PRR index may be easily integrated into existing software packages supplied by vendors of hemodynamic catheterization lab analysis that run in real time during the catheterization, thus enabling clinicians to obtain the PRR index automatically, with no added calculation time or time devoted to making any additional measurement. The PRR index described herein may be obtained using a combination of well established ECG detection algorithms, such that companies that provide software for the computers receiving the catheterization-derived hemodynamic data may utilize the PRR index to increase the versatility of the computers.

A computing device or computer such as described herein has one or more processors or processing units and a system memory. The computer typically has at least some form of computer readable media. Computer readable media, which include both volatile and nonvolatile media, removable and non-removable media, may be any available medium that may be accessed by computer. By way of example and not limitation, computer readable media comprise computer storage media and communication media. Computer storage media include volatile and nonvolatile, removable and non-removable media implemented in any method or technology for storage of information such as computer readable instructions, data structures, program modules or other data. For example, computer storage media include RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium that may be used to store the desired information and that may be accessed by computer. Communication media typically embody computer readable instructions, data structures, program modules, or other data in a modulated data signal such as a carrier wave or other transport mechanism and include any information delivery media. Those skilled in the art are familiar with the modulated data signal, which has one or more of its characteristics set or changed in such a manner as to encode information in the signal. Wired media, such as a wired network or direct-wired connection, and wireless media, such as acoustic, RF, infrared, and other wireless media, are examples of communication media. Combinations of any of the above are also included within the scope of computer readable media.

Although described in connection with an exemplary computing system environment, embodiments of the invention are operational with numerous other general purpose or special purpose computing system environments or configurations. The computing system environment is not intended to suggest any limitation as to the scope of use or functionality of any aspect of the invention.

Embodiments of the invention may be described in the general context of computer-executable instructions, such as program modules, executed by one or more computers or other devices. The computer-executable instructions may be organized into one or more computer-executable components or modules. Generally, program modules include, but are not limited to, routines, programs, objects, components, and data structures that perform particular tasks or implement particular abstract data types. Aspects of the invention may be implemented with any number and organization of such components or modules. For example, aspects of the invention are not limited to the specific computer-executable instructions or the specific components or modules illustrated in the figures and described herein. Other embodiments of the invention may include different computer-executable instructions or components having more or less functionality than illustrated and described herein. Aspects of the invention may also be practiced in distributed computing environments where tasks are performed by remote processing devices that are linked through a communications network. In a distributed computing environment, program modules may be located in both local and remote computer storage media including memory storage devices.

In operation, a computer executes computer-executable instructions embodied in one or more computer-executable components stored on one or more computer-readable media to implement aspects of the invention described and/or illustrated herein.

The order of execution or performance of the operations in embodiments of the invention illustrated and described herein is not essential, unless otherwise specified. That is, the operations may be performed in any order, unless otherwise specified, and embodiments of the invention may include additional or fewer operations than those disclosed herein. For example, it is contemplated that executing or performing a particular operation before, contemporaneously with, or after another operation is within the scope of aspects of the invention.

When introducing elements of aspects of the invention or the embodiments thereof, the articles "a," "an," "the," and "said" are intended to mean that there are one or more of the elements. The terms "comprising," "including," and "having" are intended to be inclusive and mean that there may be additional elements other than the listed elements.

Having described aspects of the invention in detail, it will be apparent that modifications and variations are possible without departing from the scope of aspects of the invention as defined in the appended claims. As various changes could be made in the above constructions, products, and methods without departing from the scope of aspects of the invention, it is intended that all matter contained in the above description and shown in the accompanying drawings shall be interpreted as illustrative and not in a limiting sense.

What is claimed is:

1. A method for assessing cardiac function, said method comprising:
   obtaining ventricular pressure data from a subject during an invasive cardiac procedure, said received pressure data comprising a diastatic ventricular pressure value, a minimum ventricular pressure value, and a predefined fiducial marker pressure value;

determining a first pressure difference between the received diastatic ventricular pressure value and the received minimum ventricular pressure value;

determining a second pressure difference between the received fiducial marker pressure value and the received minimum ventricular pressure value, wherein the fiducial marker pressure value corresponds to one or more of the following: an end diastolic pressure value, and a pressure value at the steepest slope of a pressure contour derived from the ventricular pressure data;

comparing the first pressure difference with the second pressure difference to generate an index value indicative of early diastolic cardiac function, wherein the index value is based on a ratio of the first pressure difference to the second pressure difference; and providing the generated index value to a health care provider to provide an assessment of cardiac function in the subject.

2. The method of claim 1, wherein said determining the first pressure difference, said determining the second pressure difference, said comparing, and said providing occur during or after the invasive cardiac procedure to enable the health care provided to dynamically assess cardiac function.

3. The method of claim 1, wherein receiving the ventricular pressure data comprises receiving left ventricular pressure data sampled over time.

4. The method of claim 1, wherein the generated index is based on one or more of the following: ventricular diastolic function, ventricular viscoelasticity, ventricular relaxation, presence or absence of a delayed relaxation pattern, valvular function, ventricular efficiency, and ventricular energetics.

5. The method of claim 1, wherein receiving the ventricular pressure data comprises receiving running averages of each of the diastatic ventricular pressure value, the minimum ventricular pressure value, and the predefined fiducial marker pressure value.

6. The method of claim 1, wherein obtaining ventricular pressure data comprises receiving a first set of ventricular pressure data, said method further comprising:

storing the generated index;

obtaining a second set of ventricular pressure data from the subject;

determining the first and second pressure differences as a function of the received second set of ventricular pressure data;

comparing the first and second pressure differences to generate a second index value;

averaging the index value and the second index value; and providing the averaged index value to the health care provider.

* * * * *